(12) United States Patent
Alshami

(10) Patent No.: US 11,024,195 B2
(45) Date of Patent: Jun. 1, 2021

(54) DIAGNOSTIC AND THERAPEUTIC SYSTEM FOR MANUAL THERAPY

(71) Applicant: Imam Abdulrahman Bin Faisal University, Dammam (SA)

(72) Inventor: Ali Muteb Y. Alshami, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 378 days.

(21) Appl. No.: 15/949,332

(22) Filed: Apr. 10, 2018

(65) Prior Publication Data
US 2019/0311648 A1    Oct. 10, 2019

(51) Int. Cl.
| | | |
|---|---|---|
| G09B 19/00 | (2006.01) | |
| G09B 5/04 | (2006.01) | |
| G09B 5/02 | (2006.01) | |
| A41D 1/00 | (2018.01) | |
| A41D 19/00 | (2006.01) | |
| A61B 5/11 | (2006.01) | |
| A61B 5/00 | (2006.01) | |
| A61H 1/00 | (2006.01) | |

(52) U.S. Cl.
CPC .......... *G09B 19/003* (2013.01); *A41D 1/002* (2013.01); *A41D 19/0027* (2013.01); *G09B 5/02* (2013.01); *G09B 5/04* (2013.01); *A61B 5/1121* (2013.01); *A61B 5/6806* (2013.01); *A61B 2505/09* (2013.01); *A61B 2560/0214* (2013.01); *A61B 2562/0261* (2013.01); *A61H 1/008* (2013.01); *A61H 2205/102* (2013.01)

(58) Field of Classification Search
CPC ........ G09B 19/00; G09B 19/003; G09B 5/02; G09B 5/04; A41D 1/002; A41D 19/0027; A61B 5/1121; A61B 5/6806; A61B 2505/09; A61B 2560/2514; A61B 2562/0261; A61B 2560/0214; A61H 1/008; A61H 2205/102
See application file for complete search history.

(56) References Cited

U.S. PATENT DOCUMENTS

| | | | |
|---|---|---|---|
| 10,065,074 B1 * | 9/2018 | Hoang | G16H 40/63 |
| 2010/0198115 A1 | 8/2010 | Koeneman et al. | |
| 2019/0117156 A1 * | 4/2019 | Howard | A61B 5/0024 |

FOREIGN PATENT DOCUMENTS

WO    2017/171660 A1    10/2017

OTHER PUBLICATIONS

McQuade, Kevin, et al.; Objective assessment of joint stiffness: A clinically oriented hardware and software device with an application to the shoulder joint; Aug. 30, 2012; pp. 1-20; https://www.ncbi.nlm.nih.gov/pmc/articles/PMC3639440/.

Björnsdóttir SV, et al.; Posterior-anterior(PA) pressure puffin for measuring and treating spinal stiffness: Mechanism and repeatability; Apr. 22, 2016; pp. 1-2; https://www.ncbi.nlm.nih.gov/pubmed/26559318.

* cited by examiner

*Primary Examiner* — Timothy A Musselman
(74) *Attorney, Agent, or Firm* — Oblon, McClelland, Maier & Neustadt, L.L.P.

(57) ABSTRACT

The present disclosure relates to a system for joint mobilization comprising a mobilization tool, a head unit, and a mobilization glove. The system is directed to relief for patients suffering from joint pain and stiffness. The system provides for a controlled approach to evaluation and treatment of joint pain and stiffness, allowing for universal implementation while minimizing inter-therapist error. Moreover, the system provides for adapting longitudinal patient care.

20 Claims, 12 Drawing Sheets

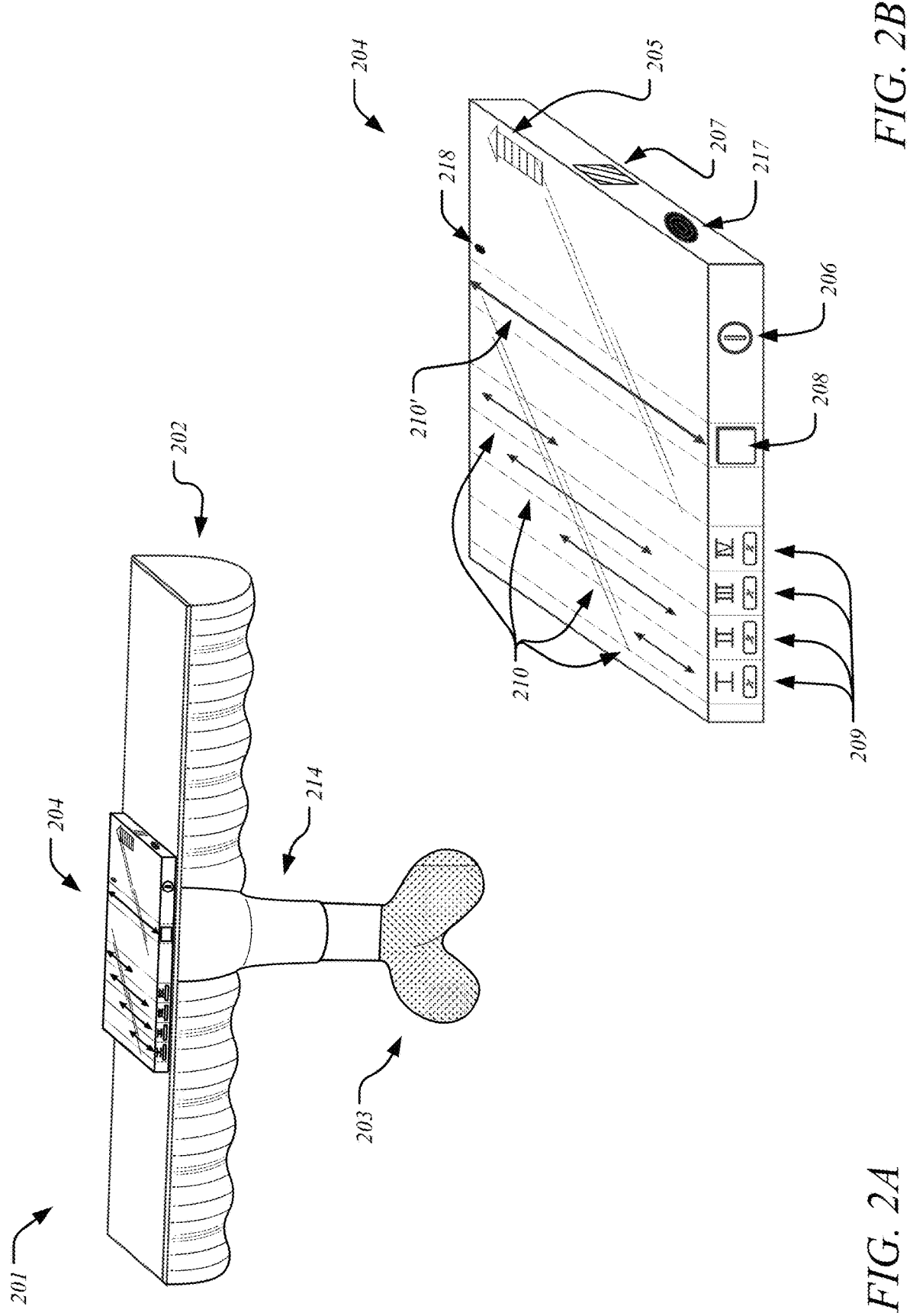

DIAGNOSTIC AND THERAPEUTIC SYSTEM FOR MANUAL THERAPY

BACKGROUND

Field of the Disclosure

The present disclosure is related to a system for treating musculoskeletal pain and related disability, comprising tools for evaluating joint range of motion and providing targeted manual therapy.

DESCRIPTION OF THE RELATED ART

Manual therapy methods are often used by physical therapists in the treatment of pain syndromes, including spinal pain. In a technique known as posteroanterior mobilization, therapists use their hands or thumbs to push down on a lumbar vertebra of a patient lying in prone. Similar approaches, including those where pressure is applied from different directions, may be applied to joints of the extremities, such as the knee. These manual therapy techniques fall into four categories. First, pressure may be applied by the thumbs, thereby transferring pressure through the pads of the thumbs positioned above a joint. Second, the hypothenar area of the palm of the hand (i.e., pisiform grip) may be used in order to apply larger forces to stiffer joints, an approach often required during mobilization of the spine. Third, the tips of the fingers may be used to apply pressure to smaller extremity joints. And fourth, a web space grip technique using the lateral aspect of metacarpophalangeal joint may be employed for other, specific joints, including the elbow.

In each approach, the amplitude of movement used in treatment is determined by the therapist's assessment of the patient's joint stiffness. This assessment is then deployed in an effort to apply a consistent force to the patient's joint, thereby generating a target displacement. The manual therapist's hands, therefore, have to be both sensitive to small differences in stiffness and also force-absorbing over an extended period of use. Because these demands may be contradictory, in that the continual force absorption during mobilization may impact the ability of the therapist to sense differences in stiffness, devices have been developed to eliminate the subjective role of the therapists' hands to ensure objectively-applied, controlled levels of force. While devices, such as a mobilizing dynamometer, provide a two-handed approach or a force dial allows therapists to monitor force application during therapy, thus ensuring appropriate levels of joint mobilization, patients often expect human touch from therapists. The use of a cumbersome tool or device in manual therapy inevitably affects the sensation of touch experienced by the patient, thus rendering these tools unsuitable for clinical practice.

In light of the above, an ideal approach to joint mobilization combines the objective force application of dynamometers and other, similar devices with a patient-friendly approach mimicking the hand-based, clinical techniques used by therapists during force application.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to an apparatus, method and system for joint mobilization.

According to an embodiment, the present disclosure relates to an apparatus for joint mobilization, comprising one or more sensors, one or more alert components, and a processing circuitry configured to receive, from the one or more sensors, a first sensed data in response to a first applied motion to a joint of a patient, determine, based upon the first sensed data, a range of motion of the joint of the patient, receive, from the one or more sensors, a second sensed data in response to a second applied motion to the joint of the patient, determine, based upon the second sensed data and the range of motion of the joint of the patient, a relative magnitude of the second sensed data of the second applied motion to the joint of the patient, and generate, based upon the relative magnitude of the second sensed data of the second applied motion to the joint of the patient, a signal to the one or more alert components indicating the relative magnitude of the second sensed data of the second applied motion to the joint of the patient.

According to an embodiment, the present disclosure relates to the apparatus for joint mobilization described above, wherein the one or more sensors include force sensors, accelerometers, gyroscopes, or a combination thereof.

According to an embodiment, the present disclosure relates to the apparatus for joint mobilization described above, wherein the force sensors include strain gauges, piezo-resistive elements, or a combination thereof.

According to an embodiment, the present disclosure relates to the apparatus for joint mobilization described above, wherein the first sensed data and the second sensed data are displacement data.

According to an embodiment, the present disclosure relates to the apparatus for joint mobilization described above, wherein the one or more alert components includes a light-emitting diode, a haptic motor, or a combination thereof.

According to an embodiment, the present disclosure relates to the apparatus for joint mobilization described above, wherein the processing circuitry is further configured to identify, based upon the first sensed data, a target motion of the range of motion of the joint of the patient, determine, based upon the second sensed data and the target motion of the range of motion of the joint of the patient, the accuracy of the second applied motion to the joint of the patient, and generate, via the processing circuitry, a signal to the one or more alert components indicating the accuracy of the applied motion to the joint of the patient.

A method for joint mobilization, comprising receiving, from a one or more sensors, a first sensed data in response to a first applied motion to a joint of a patient, determining, via a processing circuitry, based upon the first sensed data, a range of motion of the joint of the patient, receiving, from the one or more sensors, a second sensed data in response to a second applied motion to the joint of the patient, determining, via the processing circuitry, based upon the second sensed data and the range of motion of the joint of the patient, a relative magnitude of the second sensed data of the second applied motion to the joint of the patient, and generating, via the processing circuitry, based upon the relative magnitude of the second sensed data of the second applied motion to the joint of the patient, a signal to an alert component hardware indicating the relative magnitude of the second sensed data of the second applied motion to the joint of the patient.

According to an embodiment, the present disclosure relates to the method for joint mobilization described above, wherein the one or more sensors include force sensors, accelerometers, gyroscopes, or a combination thereof.

According to an embodiment, the present disclosure relates to the method for joint mobilization described above, wherein the force sensors include strain gauges, piezo-resistive elements, or a combination thereof.

According to an embodiment, the present disclosure relates to the method for joint mobilization described above, wherein the first sensed data and the second sensed data are displacement data.

According to an embodiment, the present disclosure relates to the method for joint mobilization described above, wherein the one or more alert components includes a light-emitting diode, a haptic motor, or a combination thereof.

According to an embodiment, the present disclosure relates to the method for joint mobilization described above, further comprising identifying, via the processing circuitry and based upon the first sensed data, a target motion of the range of motion of the joint of the patient, determining, via the processing circuitry, based upon the second sensed data and the target motion of the range of motion of the joint of the patient, the accuracy of the second applied motion to the joint of the patient, and generating, via the processing circuitry, a signal to the one or more alert components indicating the accuracy of the applied motion to the joint of the patient.

A system for joint mobilization, comprising a mobilization tool having a first processing circuitry configured to transmit a sensed data from a first set of one or more sensors, a head unit having a second processing circuitry, and a mobilization glove having a third processing circuitry configured to receive and process sensed data from the head unit, and receive, process, and transmit sensed data from a second set of one or more sensors, wherein the second processing circuitry is configured to receive, process, store, and transmit sensed data from the mobilization tool, the mobilization glove, or a combination thereof.

According to an embodiment, the present disclosure relates to the system for joint mobilization described above, wherein the first set of one or more sensors and the second set of one or more sensors include force sensors, accelerometers, gyroscopes, or a combination thereof.

According to an embodiment, the present disclosure relates to the system for joint mobilization described above, wherein the force sensors include strain gauges, piezoresistive elements, or a combination thereof.

According to an embodiment, the present disclosure relates to the system for joint mobilization described above, wherein the mobilization glove further comprises alert components.

According to an embodiment, the present disclosure relates to the system for joint mobilization described above, wherein the alert components include a display, a speaker, a haptic motor, or a combination thereof.

According to an embodiment, the present disclosure relates to the system for joint mobilization described above, wherein the second processing circuitry is configured to receive, from the mobilization tool, a first sensed data in response to an applied motion to a joint of a patient, determine, based upon the first sensed data, a range of motion of the joint of the patient, identify, based upon the first sensed data, a target motion of the range of motion of the joint of the patient, transmit, to the mobilization glove, the target motion of the range of motion of the joint of the patient, receive, from the third processing circuitry, a second sensed data in response to an applied motion to the joint of the patient, determine, based upon the second sensed data and the target motion of the range of motion of the joint of the patient, the accuracy of an applied motion to the joint of the patient, and generate, via the third processing circuitry, a signal to an alert component indicating the accuracy of the applied motion to the joint of the patient.

According to an embodiment, the present disclosure relates to the system for joint mobilization described above, wherein the first sensed data and the second sensed data are displacement data.

According to an embodiment, the present disclosure relates to the system for joint mobilization described above, wherein the mobilization tool, the head unit, and the mobilization glove are in wireless communication.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 2A is a perspective view of a mobilization tool, according to an embodiment of the present disclosure;

FIG. 2B is a perspective view of a head unit of the mobilization tool, according to an embodiment of the present disclosure;

DETAILED DESCRIPTION

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "the processing circuitry" of the mobilization tool, head unit, and mobilization glove recognizes the duplicative functionality of certain features of these aspects of the present disclosure. Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

Figure 1:
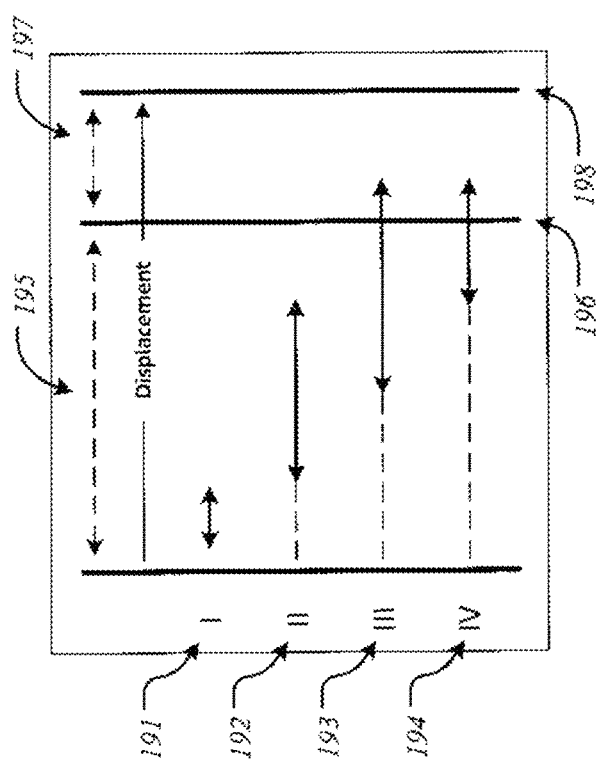
FIG. 1 is a graphical display of established grades of joint mobility.

Joint mobilization is a manual technique widely used by clinicians, particularly physical therapists, in the examination and treatment of patients with pain syndromes of the spine and extremities. This technique is usually passive, meaning that the patient does not activate musculature in order to produce motion. Instead, a therapist applies a force to a specific location at a joint of interest, resulting in motion, or displacement, of one portion of a joint with respect to another. In an example, in the knee joint, force may be applied to the tibia, thereby producing a displacement of the tibia relative to the femur. This displacement of the tibia relative to the femur indicates a range of motion of the knee joint of the patient, and is reflective of the health of the joint and the pain syndromes of the patient. This passive motion typically has two forms: 1) rhythmic oscillations or sustained force in different positions of a range of movement, and 2) high velocity thrusts near the limit of range of movement. Depending on the targeted treatment, these movements may be performed in different positions in the range and/or use movements of small or large amplitude. These movements are divided in to grades, as described in FIG. 1. FIG. 1 is a graphical display of established grades of joint mobility. During use of the mobilization tool or the mobilization glove of the present disclosure, the distance between rest and an anatomic limit 198 is divided into gradations. These gradations include Grade I 191, reflecting initial movement within a range of available joint play 195, Grade II 192 reflecting movement midrange, Grade III 193, reflecting additional movement beyond the range of available joint play 195, surpassing initial tissue resistance 196 and entering into a stretch region 197, and Grade IV 194, similarly existing at the edge of the range of available joint play 195, surpassing initial tissue resistance 196 and reaching towards the anatomic limit 198. Applied to a patient, and according to the Maitland Joint Mobilization Grading Scale, Grade I 191 reflects small amplitude rhythmic oscillating mobilization in early range of movement, Grade II 192 reflects large amplitude rhythmic oscillating mobilization in midrange of movement, Grade III 193 reflects large amplitude rhythmic oscillating mobilization to a point of limitation in the range of movement, and Grade IV 194 reflects small amplitude rhythmic oscillating mobilization at end-range of movement. The application of a specific grade of movement is critical to the therapy and rehabilitation of patients suffering from joint pain or stiffness. Current techniques, however, rely on subjective determinations of joint movement, failing to efficiently determine desired mobilization grades and, therefore, provide relief for patients suffering from pain and/or an impaired joint range of movement.

FIG. 2, therefore, is an illustration of a mobilization tool for the controlled, objective application of force to a joint. FIG. 2A is a perspective view of a mobilization tool, according to an embodiment of the present disclosure. In an exemplary embodiment, the mobilization tool is a spinal mobilization tool 201. The spinal mobilization tool 201 includes a grip 202. In an embodiment, and in a nonlimiting manner, the grip 202 is of an ergonomic design allowing for efficient force transfer and minimal hand strain while allowing access to a data unit 204. The grip 202 can be at any position relative to the direction of applied motion, or applied force, including but not limited to coincident and perpendicular. The grip 202 is connected to a probe 203 via a tool adapter 214. The probe 203 may be an interchangeable probe and of a design specific to the joint of interest. During operation, the probe 203 may be rigidly fixed to the tool adapter 214 via techniques known in the art, including threaded surfaces. The tool adapter 214 provides a communication port between the probe 203 and the data unit 204. The communication port further houses sensors for measuring the forces encountered at the probe 203. Force data generated by the sensors in response to externally applied forces at the probe 203 are transmitted to the data unit 204 via the tool adapter 214.

FIG. 2B is a perspective view of an aspect of the mobilization tool, according to an embodiment of the present disclosure. The mobilization tool may be used for the diagnosis, therapy, or a combination thereof, of joint pain conditions. In an embodiment, an inertial unit, comprising an accelerometer and gyroscope, is housed within the data unit 204. The inertial unit acquires data related to the orientation and acceleration of the mobilization unit such that displacement data may be extracted (described in FIG. 6).

According to an embodiment, the data unit 204 further comprises a user interface for establishing a patient range of motion (ROM) and, therefrom, indicating a current position within the patient's ROM. According to an embodiment, the user interface includes a tare toggle 208. During operation, upon location of boney surfaces in the joint of interest, the user may depress the tare toggle 208 in order to establish a zero displacement. In an example of the knee joint, the bony surface may be a tibial tuberosity, wherein a force applied to the tibial tuberosity produces displacement of the tibia relative to the femur. This zero displacement reflects the position at which the user is in direct contact with a bone (e.g. tibia) of the joint, having palpated through layers of soft tissue (e.g. skin, muscle) that might otherwise obfuscate results. Following mobilization of a joint to the anatomic limit, the user may again depress the tare toggle 208 to establish a full ROM. In another embodiment, a zero displacement may be indicated by a rapid elevation in force measured by the force sensor of the mobilization tool, wherein the rapid elevation is above a pre-determined threshold at which bony contact is presumed.

The difference between zero displacement and full displacement reflects a passive range of motion of the joint and is determined by a processing circuitry, which may be local or remote. The local or remote processing circuitry further processes the displacement data to divide the ROM into gradations (or Grades I-IV). During mobilization, visual indicators, or alert components, of the current Grade of mobilization are presented on one or more surfaces of the data unit 204. According to an embodiment, the visual indicators include but are not limited to light emitting diodes (LEDs). On a first of the one or more surfaces, LED indicators 209 provide confirmation that the user is within a specific range. On a second of the one or more surfaces, indicators 210 are LED indicators underlying arrows providing guidance similar to the graphic of FIG. 1. For example, during a Grade III mobilization, large amplitude oscillations at the mid-range to end range of ROM are indicated as illuminated arrows. In another embodiment, the indicators 210 are reference arrows engraved on the second of the one or more surfaces of the data unit 204. An indicator 210' is a visual reference against which the intended action suggested by the indicators 210 may be compared.

In an embodiment, the data unit 204 includes a processing circuitry configured to receive, process, output, and transmit data generated by the sensing components. In another embodiment, the processing circuitry of the data unit 204 is only sufficient to control the transmission of data to and from a head unit via a wireless communication unit 207, wherein the head unit comprises a processing circuitry configured to receive, process, store, and transmit data generated by the sensing components of the mobilization tool 201. The wireless communication unit 207 comprises modalities known in the art including but not limited to millimeter wave radiofrequency, Bluetooth, and Wi-Fi.

According to an embodiment, a power toggle/indicator 206 and battery depletion indicator 205, with reference to a battery, are provided on the data unit 204. The battery may be a disposable or a rechargeable battery. In an exemplary embodiment, the battery is a rechargeable battery that may be energized by a variety of techniques including but not limited to conduction and induction.

According to an embodiment, a haptic motor 217 is disposed in the data unit 204. During operation of the mobilization tool 201, the haptic motor 217 may be excited by the processing circuitry as negative feedback to the user regarding mobilization of the joint. For example, if it is determined that the user is applying insufficient force to a joint in context of a target Grade of therapy, a vibratory sensation may be supplied by the haptic motor 217 to alert the user of the relative error.

Further, according to an embodiment, a speaker 218 is supplied within the data unit 204 to alert the user of actions related to joint mobilization. Alerts may be audible tones or pre-determined sounds or phrases to inform the user that a correct motion is performed or to provide negative feedback so that the user can modify force application. The speaker 218, via the local or remote processing circuitry, may further provide spoken language alerts or commands to the user.

According to an embodiment, the processing circuitry is configured to provide signals to output components including the LED indicators 209, the haptic motor 217, and the speaker 218 to inform and guide the user of the mobilization tool 201 with respect to a target therapy Grade. For example, the output components may indicate to the user, initially, a target therapy Grade as prescribed by the patient's care provider, or prescribing therapist, and as determined via wireless communication with the head unit. The output components may then, as the user begins to mobilize the joint of interest, alert the user when motion is applied within the target Grade or when the motion is outside the target Grade. Flashing of the LED indicators 209, an audible alert, a vibration, or similar, may be implemented to plainly indicate to the user proper technique. Moreover, the output components, and the speaker 218, in particular, may indicate to the user a currently applied force and the force previously required in order to achieve a target Grade of mobilization, providing context for longitudinal improvement of patient joint mobility. In another embodiment, the output components of the mobilization tool 201, and the LED indicators 209, in particular, display the current Grade of mobilization, independent of a prescribed Grade from a care provider in the instance wherein the head unit is not used to prescribe a Grade.

Figures 3A, 3B:
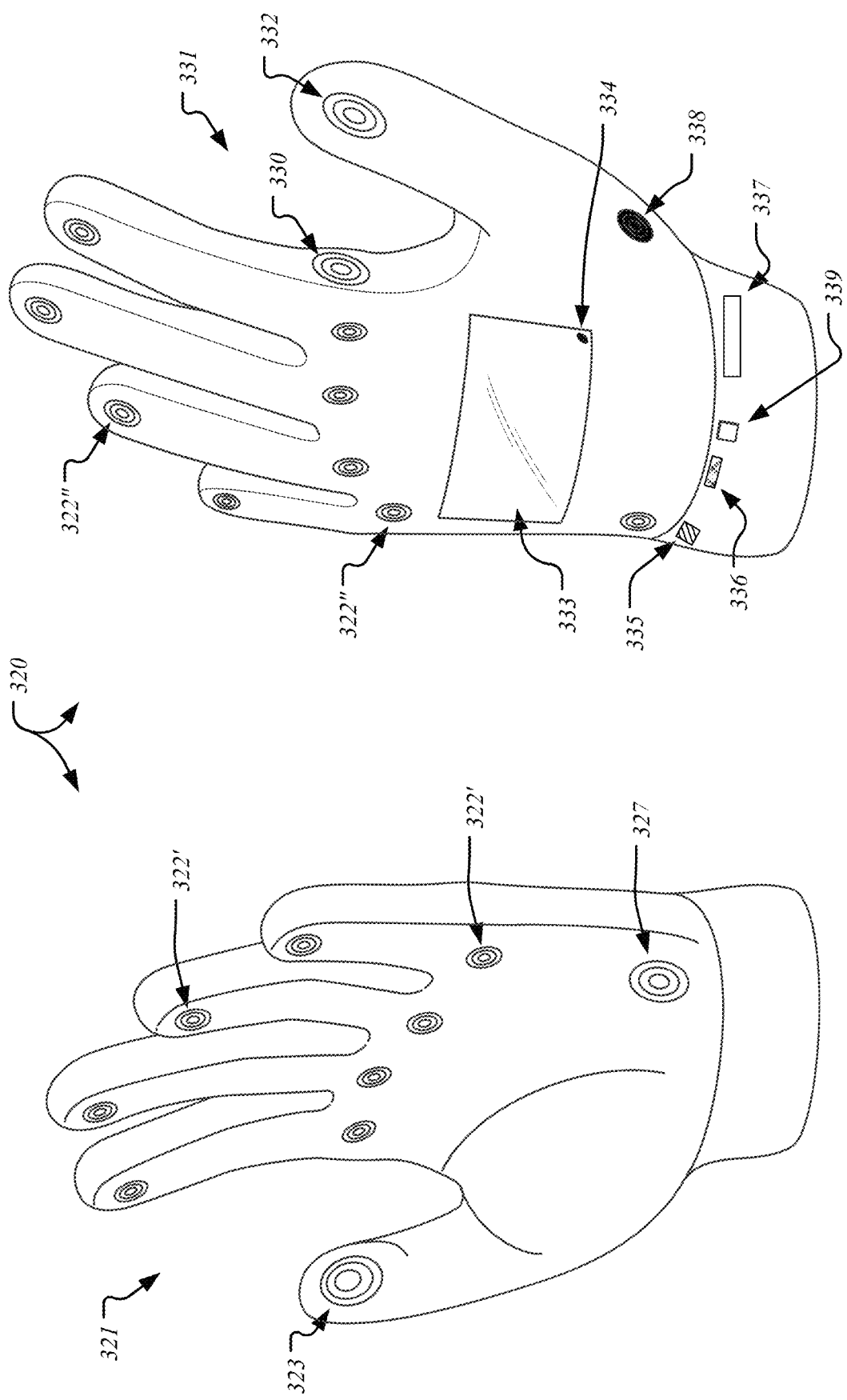
FIG. 3A is a perspective view of a palmar aspect of a mobilization glove, according to an embodiment of the present disclosure.
FIG. 3B is a perspective view of a dorsal aspect of the mobilization glove, according to an embodiment of the present disclosure.

FIG. 3 is a perspective view of a mobilization glove for use in joint mobilization. Similar to the mobilization tool, the mobilization glove may be used for the diagnosis, therapy, or a combination thereof, of joint pain conditions. According to an embodiment, the mobilization glove 320 is of a material including but not limited leather, elastic polyurethane, neoprene, cotton, polyester, acrylic, and nylon, and of a thickness sufficient to house a variety of circuit elements and hardware components. To this end, FIG. 3A is a perspective view of a palmar aspect 321 of the mobilization glove 320, according to an embodiment of the present disclosure. At tactile positions of the palmar aspect of the glove, including the metacarpophalangeal joints 322', the hypothenar eminence 327, and the tips of the digits, sensors for data acquisition are disposed. In an exemplary embodiment, the palmar sensors 322' include a force sensor 323. Opposite the position of the palmar sensors 322', on the dorsal aspect 331 of the mobilization glove 320, are disposed additional sensors for data acquisition. FIG. 3B is a perspective view of a dorsal aspect of the mobilization glove.

According to an embodiment of the present disclosure, dorsal sensors 322" comprise an inertial unit 332 for the collection of data related to the orientation and acceleration of the glove via accelerometer and gyroscope. Moreover, this data may be specifically related to the orientation and acceleration of the palmar sensors 322'.

According to an embodiment, an additional sensor 330 is disposed in the web space of the mobilization glove 320. The sensor 330 may comprise a force sensor, an inertial unit, or a combination thereof.

In an embodiment, a processing circuitry 336 is disposed on the dorsal aspect 331 of the mobilization glove 320 and is configured to receive, process, output, and transmit data generated by the sensing components of the palmar aspect 321 and dorsal aspect 331 of the mobilization glove 320. In another embodiment, the processing circuitry 336 is only sufficient to control the transmission of data to and from a head unit via a wireless communication unit 335, wherein the head unit comprises a processing circuitry configured to receive, process, store, and transmit data generated by the sensing components of the mobilization glove 320. The wireless communication unit 335 comprises modalities known in the art including but not limited to millimeter wave radiofrequency, Bluetooth, and Wi-Fi.

Following data acquisition from sensors disposed on the palmar aspect 321 and the dorsal aspect 331 of the mobilization glove 320, the local processing circuitry 336 or remote processing circuitry, via the wireless communication unit 335, process and output appropriate signals to features of the dorsal aspect 331 of the mobilization glove 320.

At the proximal end of the thumb, at the basal carpometacarpal joint, is disposed a haptic motor 338. During operation of the mobilization glove 320, the haptic motor 338 may be excited by the processing circuitry as negative feedback to the user regarding mobilization of the joint. For example, if it is determined that the user is applying insufficient force to a joint in context of a target Grade of therapy, a vibratory sensation may be supplied by the haptic motor 338 to alert the user of the relative error.

According to an embodiment, a tare toggle 339 is disposed on the dorsal aspect 331 of the mobilization glove 320. During operation, upon location of boney surfaces at the joint of interest, the user may depress the tare toggle 339 in order to establish a zero displacement. In an example of the knee joint, the bony surface may be a tibial tuberosity, wherein a force applied to the tibial tuberosity produces displacement of the tibia relative to the femur. This zero displacement reflects the position at which the user is in direct contact with a bone (e.g. tibia) of the joint, having palpated through layers of soft tissue (e.g. skin, muscle) that might otherwise confuse results. Following mobilization of a joint to the anatomic limit, the user may again depress the tare toggle 339 to establish a full ROM. In another embodiment, a zero displacement may be indicated by a rapid elevation in force measured by the force sensors of the mobilization glove, wherein the rapid elevation is above a pre-determined threshold at which bony contact is presumed.

The difference between zero displacement and full displacement is determined by the processing circuitry, which may be local 336 or remote. The local 336 or remote processing circuitry further processes the displacement data to divide the ROM into gradations (or Grades I-IV). During mobilization, visual indicators, or alert components, of the current Grade of mobilization are presented via the output components of the mobilization glove 320. For example, during a Grade III mobilization, large amplitude oscillations at the mid-range to end range of ROM are indicated visually, audibly, or as a combination thereof.

According to an embodiment, a display 333 is disposed on the dorsal aspect 331 of the mobilization glove 320. The processing circuitry is configured to provide signals to the display 333 to inform and guide the user of the mobilization glove 320 with respect to a target therapy Grade. For example, the display 333 may indicate to the user, initially, a target therapy Grade as prescribed by the patient's care provider, or prescribing therapist, and as determined via wireless communication with the head unit. The display 333 may then, as the user begins to mobilize the joint of interest, alert the user when motion is applied within the target Grade or when the motion is outside the target Grade. A binary green/red screen, or similar, may be implemented to plainly indicate to the user proper technique. Moreover, the display 333 may indicate to the user a currently applied force and the force previously required in order to achieve a target Grade of mobilization, providing context for longitudinal improvement of patient joint mobility. In another embodiment, the display 333 of the mobilization glove 320 displays the current Grade of mobilization, independent of a prescribed Grade from a care provider in the instance wherein the head unit is not used to prescribe a Grade.

Further, according to an embodiment, a speaker 334 is supplied within the display 333 to alert the user of actions related to joint mobilization. Alerts may be audible tones or pre-determined sounds or phrases to inform the user that a correct motion is performed or to provide negative feedback so that the user can modify force application. The speaker 334, via the local 336 or remote processing circuitry, may further provide spoken language alerts or commands to the user.

According to an embodiment, a battery 337 is provided on the dorsal aspect 331 of the mobilization glove. The battery may be a disposable or a rechargeable battery. Battery depletion may be indicated via the display 333.

According to an embodiment, and in addition to the display 333 of the mobilization glove 320, visual data related to a therapy session can be communicated via a head unit comprising a display, wherein the head unit includes but is not limited to a mobile device, smartphone, tablet, and computer. Further, according to an embodiment, and in addition to the speaker 334 of the mobilization glove 320, audio related to a therapy session can be communication via a head unit comprising a speaker, wherein the head unit includes but is not limited to a mobile device, smartphone, tablet, and computer.

Figure 4:
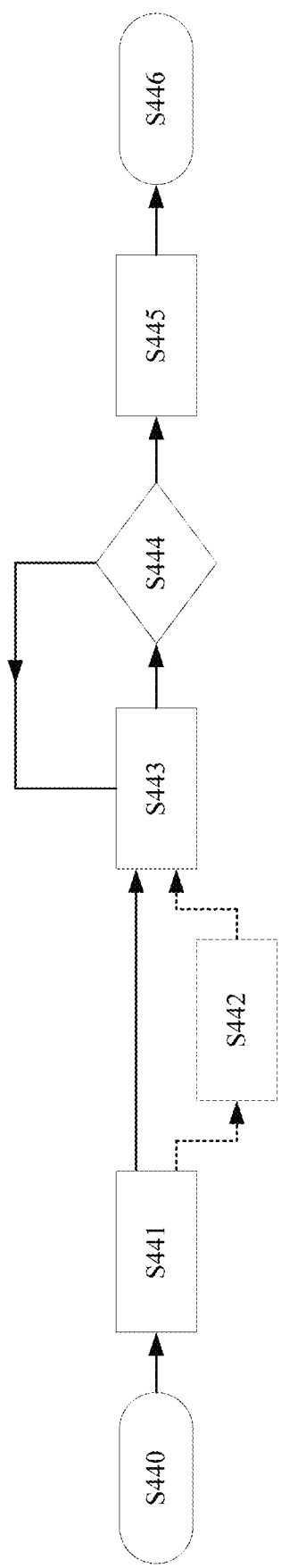
FIG. 4 is a high-level flowchart of an implementation of the mobilization tool and mobilization glove, according to an embodiment of the present disclosure.

FIG. 4 is a high-level flowchart of an implementation of a mobilization tool and mobilization glove. According to an embodiment, the mobilization tool and mobilization glove are used as a system, wherein the mobilization tool is a diagnostic tool and the mobilization glove is a therapeutic tool.

First, a patient's ROM is established S440. As related to joint mobilization, the tare toggle is depressed prior to force application to the vertebra. Following force application to that bone by the mobilization tool, the tare toggle is again depressed indicating a full displacement of the joint, or ROM. Having established the ROM, the local or remote processing circuit of the data unit or head unit then divides the ROM into Grades according to the grading scale of FIG. 1. In the context of the assigned Grades and the joint pain or stiffness experienced by the patient, a care provider or prescribing therapist recommends physical therapy with a specified target Grade S441. For example, if a patient is suffering from severe stiffness in a lumbar facet joint, a care provider may recommend initial physical therapy of Grade I, thereby applying small oscillations at low range mobilization to improve joint mobility. In an embodiment, prescription information related to the target Grade is provided verbally to a physical therapist or similar user of the mobilization glove. In another embodiment, a target Grade of physical therapy is provided by the care provider via a user interface of a head unit-based software application. Based on the data acquired wirelessly from the mobilization tool, and in context of the prescribed Grade, the head unit generates a reference force/displacement profile S442 for user feedback and for longitudinal tracking of patient mobility and improvement. With a prescribed target Grade, a user initiates a physical therapy session with a patient S443, applying force via the mobilization glove to a joint of interest. As the force is applied, the user may visually observe the display of the dorsal aspect of the mobilization glove to determine the current Grade applied in context of the target Grade S444. In another embodiment, the prescribed Grade is communicated by the head unit to the mobilization glove and feedback is provided to the user throughout the use of the mobilization glove via haptic alert, audible alert, visual alert, or a combination thereof. If an error in force application is determined visually by the user or via feedback from evaluation of the user's performance by the processing circuitry, a correction is made and force is reapplied to the joint of interest. If force application is within the target Grade, mobilization continues for the duration of the therapy session S445. At the conclusion of the therapy session, S446, data related to the mobility of the patient may be reviewed in context of the reference force/displacement profile to determine improvements in patient mobility. For example, in a therapy session, 4 psi may be required to mobilize a knee joint to Grade II. In a subsequent therapy session, only 3 psi is required to mobilize the knee joint to Grade II. This improvement can be considered by a prescribing therapist in determining if more intense therapy is warranted or how long the current Grade of therapy should be continued. In another embodiment, an evaluation of the longitudinal improvement of the user may be performed from the visually observed data on the display of the dorsal aspect of the mobilization glove. For example, displacement data from multiple therapy sessions of a user may be simultaneously displayed on the display of the dorsal aspect of the mobilization glove, demonstrating improvement of the user over time.

As the mobilization tool and mobilization glove comprise similar sensing, processing, and display elements, it should be appreciated that, in another embodiment, the mobilization tool may be used independent of the mobilization glove to perform the diagnostic and/or therapeutic functions described above. Further, it should be appreciated that, in another embodiment, the mobilization glove may be used independent of the mobilization tool to perform the diagnostic and/or therapeutic functions described above. In each embodiment, the mobilization tool or the mobilization glove may be in communication with the head unit.

Figure 5:
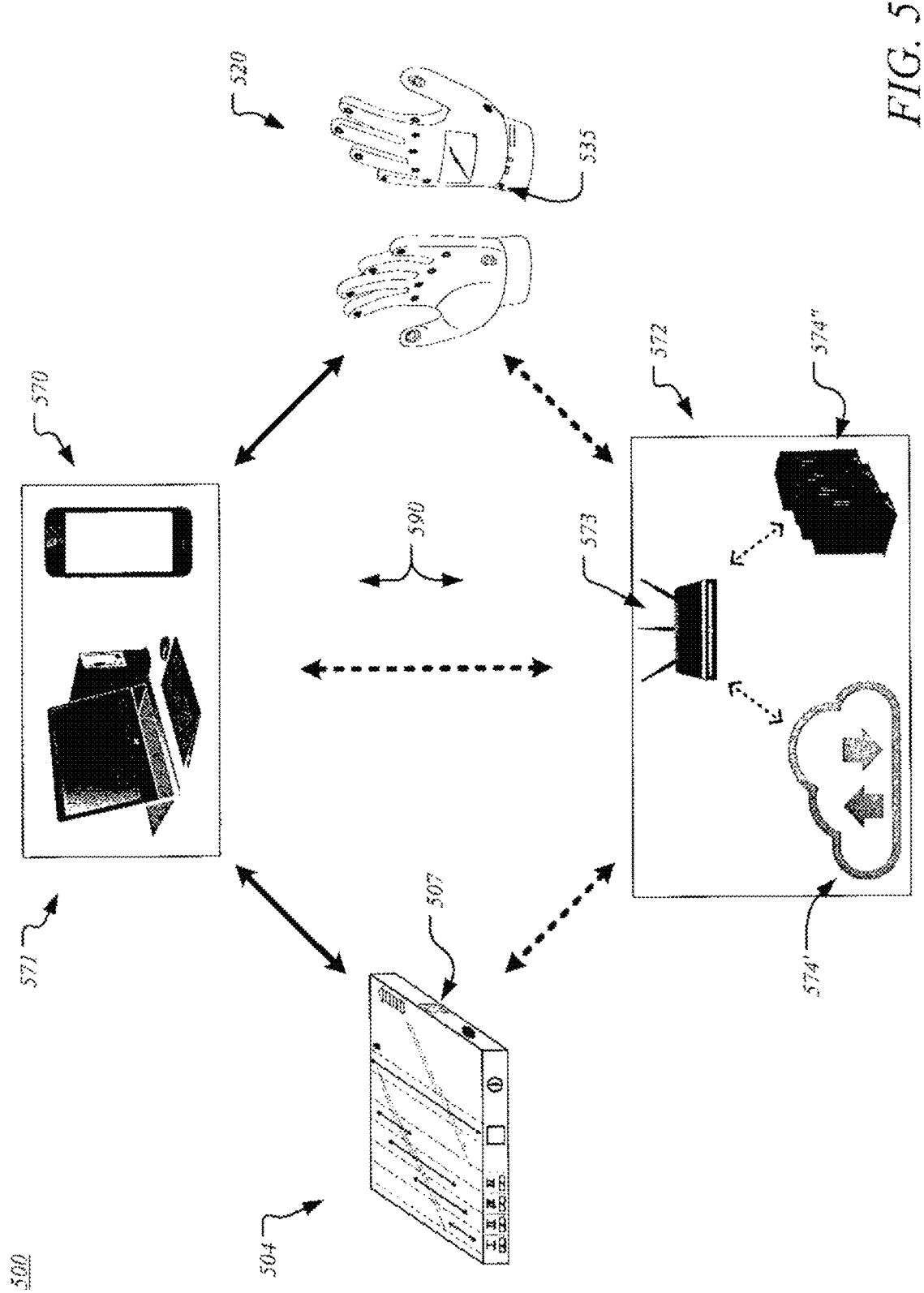
FIG. 5 is a high-level diagram of possible modes of communication amongst a mobilization tool, a head unit, and a mobilization glove, according to an embodiment of the present disclosure.

FIG. 5 is a high-level diagram of communication between a mobilization tool, a mobilization glove, and a head unit. According to an exemplary embodiment of the present disclosure, a system for joint mobilization 500 includes a mobilization tool comprising a data unit 504, a mobilization glove 520, and a head unit 590. In an embodiment, sensor data collected at the data unit 504 is communicated via the wireless communication unit 507 to the head unit 590. According to an embodiment, the head unit 590 is a local device 570 with access to local storage 571 and/or cloud storage 572. The local device 570 can be a smartphone, tablet, personal computer, CPU, or combination thereof. In addition to local storage 571, the local device 570 may access cloud storage 572. Access to local storage 571 allows for immediate data acquisition and processing while access to cloud storage 572 makes possible time-intensive longitudinal evaluation of patient performance. In another embodiment, the head unit 590 is cloud storage 572. Access to cloud storage 572 by the data unit 504 is mediated by communication between a wireless access point 573 and the wireless communications unit 507 of the data unit 504. In an embodiment, the wireless access point 573 is in communication with one or more local servers 574". In another embodiment, the wireless access point 573 is in communication with one or more remote servers 574'. Further, the head unit 590 is in communication with the mobilization glove 520 via the wireless communication unit 535.

In an embodiment, the head unit 590 is configured to operate a software application or a set of software modules to receive and send communication to and from the data unit 504 and mobilization glove 520. Similarly, the processing circuitries of the data unit 504 and the mobilization glove 520 are configured to receive and send communications to and from the head unit 590. The head unit 590 is further configured to record and track sensor-generated data from the data unit 504 and the mobilization glove 520.

In an example, the head unit 590 is a local device 570. The mobilization glove 520 acquires data regarding a therapy session of a patient. Sensor data from the session is transmitted via the wireless communication unit 535 to the local device 570. Using local storage 571, the processing circuitry of the local device 570 processes force and displacement data from the current session, in context of established Grades from the data unit 504 via the wireless communication unit 507. Simultaneously, cloud storage 572 is called in order to retrieve longitudinal data regarding patient performance during prior therapy sessions. Via the user interface of the head unit-based software application, the user may further evaluate therapist and patient performance during the therapy session.

As the mobilization tool and mobilization glove comprise similar sensing, processing, and display elements, it should be appreciated that, in another embodiment, the mobilization tool may be used independent of the mobilization glove to perform the diagnostic and/or therapeutic functions described above. Further, it should be appreciated that, in another embodiment, the mobilization glove may be used independent of the mobilization tool to perform the diagnostic and/or therapeutic functions described above. In each embodiment, the mobilization tool or the mobilization glove may be in communication with the head unit.

Figure 6:
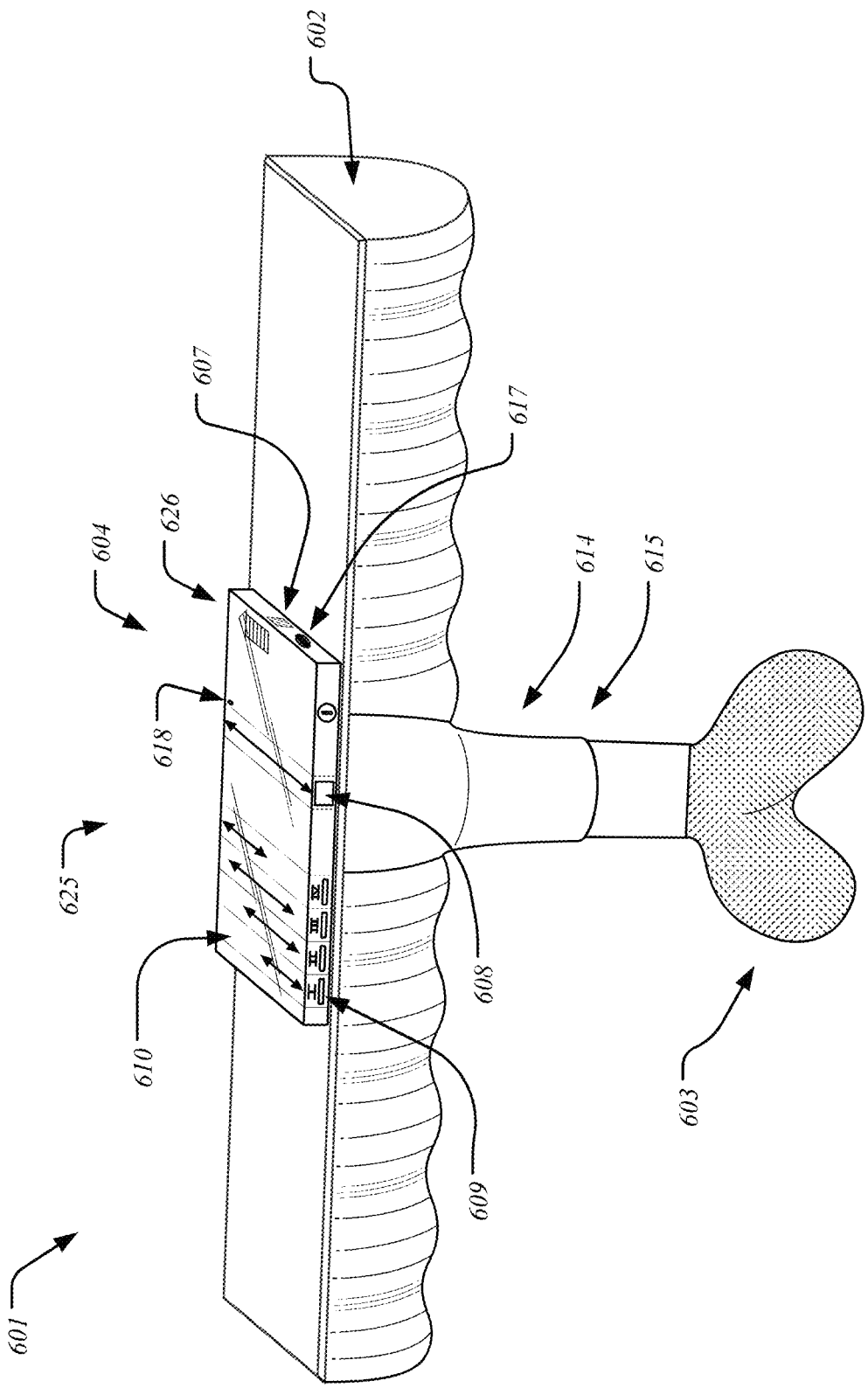
FIG. 6 is a perspective view of the hardware of the mobilization tool, according to an embodiment of the present disclosure.

FIG. 6 is a perspective view of the hardware of a mobilization tool, according to an embodiment of the present disclosure. The mobilization tool 601 includes a data unit 604, a grip 602, a tool adapter 614, and a probe 603. The probe 603 is connected to the tool adapter 614 and is in mechanical connection with a load cell 615 housed within the tool adapter 614. In an embodiment, the load cell 615 is a 136 kilogram capacity, 2-axis sub-miniature load cell, suitable for the measurement of tensile and compressive forces along an axis. Complementary to the load cell 615, and to aid in force tracking, an inertial unit 625 comprising an accelerometer/gyroscope is housed within the data unit 604, indicating the angle, velocity, acceleration, and time associated with a given task. In an embodiment, the inertial unit 625 is a MEMS 3-axis gyroscope with sensitivity up to ±2000°/second and a 3-axis accelerometer with a range up to ±16 g.

According to an embodiment, the position/motion sensor is at least one of or a combination of a geomagnetic sensor and an acceleration sensor. For example, a three-axis geomagnetic sensor ascertains the direction of geomagnetism, or in other words a geomagnetic vector Vt, given the current orientation of (the housing of) the mobilization unit 601 and data unit 604 housing the three-axis geomagnetic sensor. A three-axis acceleration sensor ascertains the direction of gravity, or in other words a gravity vector G, given the current orientation of (the housing of) the mobilization unit 604 and data unit 604 housing the 3-axis acceleration sensor in a still state. The gravity vector G matches the downward vertical direction. The gravity vector G likewise may be decomposed into Xs, Ys, and Zs axis components.

Alternatively, or additionally, a gyroscope may be used which is a sensor that detects angular velocity about the three axes Xs, Zs, and Ys (roll, pitch, and yaw), and is able to detect the rotation of an object. In addition, the geomagnetic sensor is able to ascertain the heading in which the object faces, based on a geomagnetic vector as discussed earlier.

In an exemplary embodiment, displacement of the probe 603 is determined, via the processing circuitry of the data unit 604 or the processing circuitry of the head unit, from the inertial data collected from the accelerometer and gyroscope of the inertial unit 625. Evaluating acceleration with respect to time, $\iint_{t_1}^{t_2} a = \Delta l$, where $t_1$ and $t_2$ are the time at two points and a is the acceleration of the mobilization tool, $\Delta l$ represents the quantification of the displacement of the probe and, therefore, the displacement of the bone of interest. According to an embodiment, and in a non-limiting manner, displacement of the bone of interest is typically quantified in millimeters.

Data from the load cell 615 and the inertial unit 625 are wirelessly transmitted to the head unit via the wireless communication unit 607. In an embodiment, the wireless communication unit is an IEEE 802.11 b/g compliant WiFi module with an embedded IPv4 TCP/IP stack with an SPI host interface at 16 MHz.

According to an embodiment, the inertial unit 625 of the data unit 604 is calibrated such that a primary axis is aligned with a primary axis of the load cell 615 of the tool adapter 614.

According to an embodiment, at the outset, the tare toggle 608 is used in order to establish a full ROM, or displacement, of the patient. Once the device is positioned, and prior to force application, the tare toggle 608 may be depressed in order to 'zero' both load cell and inertial unit measures. Following force application to the anatomic limit of the specified joint, the tare toggle 608 is again depressed, thereby recording a force profile associated with the required displacement to achieve full ROM. Segments within the range of motion are then, via the processing circuitry of the data unit 604 or the processing circuitry of the head unit, assigned Grades associated with therapeutic movements within the patient's ROM. In an embodiment, these Grades are represented by LED indicators 609 on one or more faces of the data unit 604. As force is applied and a displacement of the joint is induced, the LED indicators 609 of the one or more faces of the data unit 604 will illuminate the appropriate Grade. Accordingly, LED indicators 610 will illuminate an arrow on one of the one or more faces of the data unit 604 when a specified displacement is achieved, providing confirmation and training to the user of the mobilization tool 601.

According to an embodiment, the battery of the data unit 604 is a rechargeable battery 626. The rechargeable battery 626 is a thin film lithium-ion rechargeable battery that may be energized by a variety of techniques including but not limited to conduction and induction.

According to an embodiment, the speaker 618 is one of a variety of miniature speakers including but not limited to a neodymium magnet design with a Mylar cone. The haptic motor 617 is one of a variety of tactile sensors including but not limited to an Eccentric Rotating mass vibration motor.

According to an embodiment, the processing circuitry of the data unit 604 and/or the processing circuitry of the head unit are configured to determine when off-axis force application occurs. In an embodiment, the processing circuitry is further configured to generate an alert in this case. For example, the inertial unit 625 of the data unit 604 records accelerations in three-axes and, therefore, can provide data to the processing circuitry related to accelerations that may exists outside the established axis of the load cell (i.e., in line with ideal force application). In an embodiment, in order to minimize extraneous pain to the patient and protect the mobilization tool, the data unit 604 may be further outfitted with a haptic motor, or alert component, in order to alert the user of off-axis load application by providing a small vibratory stimulus to the user.

Figure 7:
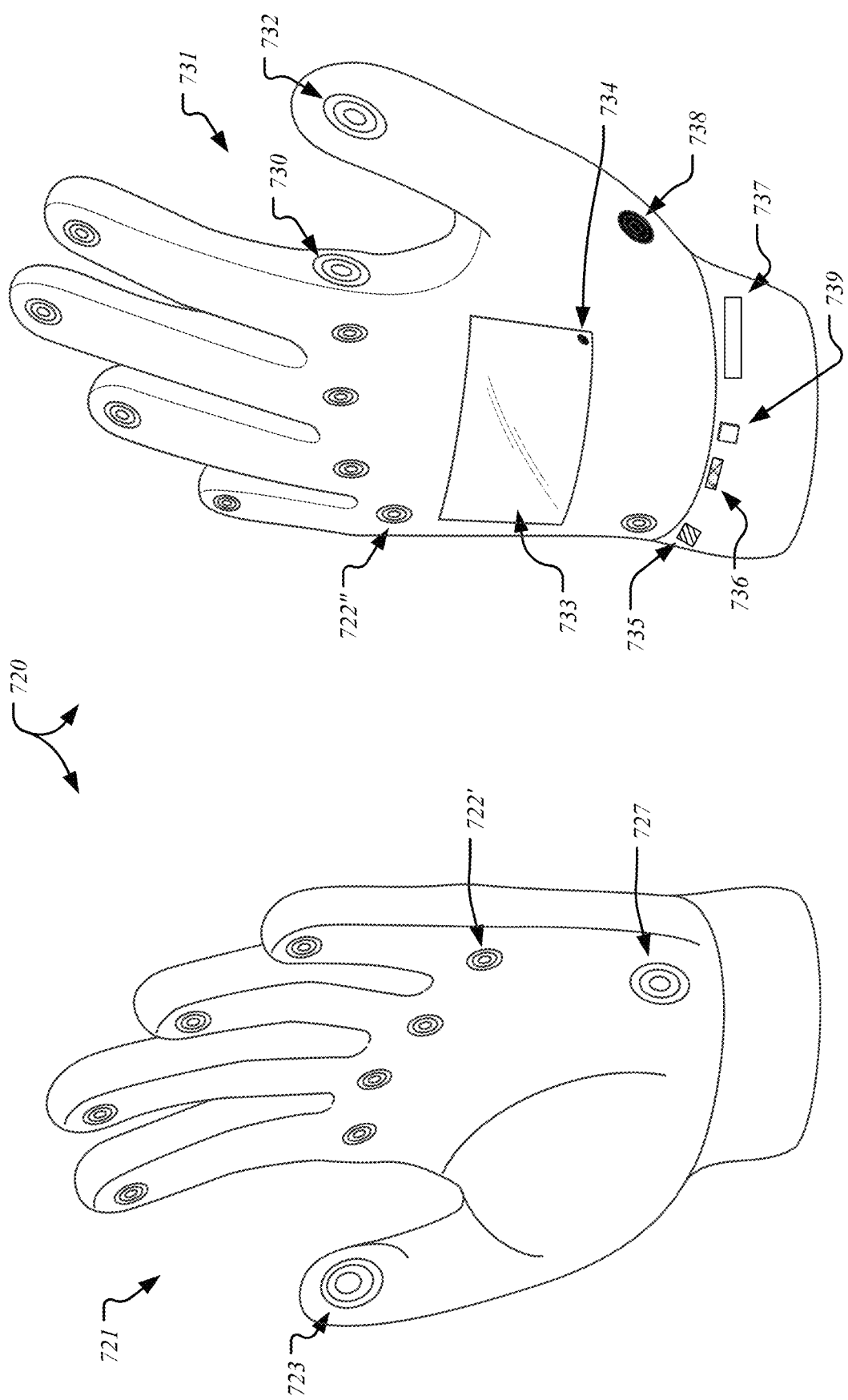
FIG. 7A is a perspective view of the hardware of a palmar aspect of the mobilization glove, according to an embodiment of the present disclosure.
FIG. 7B is a perspective view of the hardware of a dorsal aspect of the mobilization glove, according to an embodiment of the present disclosure.

FIG. 7A is a perspective view of the hardware of a palmar aspect of a mobilization glove, according to an embodiment of the present disclosure. The mobilization glove 720 may be fabricated for either the left hand or the right hand of the therapist, as desired. The palmar aspect 721 of the mobilization glove 720 includes an array of sensors at tactile positions including the metacarpophalangeal joints 722', the hypothenar eminence 727, and the tips of the digits. In an embodiment, the palmar sensors 722' include force sensors 723. The force sensors 723 may be piezo-resistive force sensors, constructed for loads up to 45 kg, whose resistance changes in step with applied pressure. In an example, a therapist applies a force to a spinous process of a cervical joint with the thumb. As load is applied to the thumb, the pressure against the sensor 723 reduces the resistance of the sensor, accordingly, and the relationship therein can be quantified. Palmar sensors 722', including force sensors 723, are in electrical communication with a processing circuitry located on a proximal portion of the mobilization glove 720. Similar to the palmar aspect 721 of the mobilization glove 720, the dorsal aspect 731 of the mobilization glove 720 includes sensors 722" disposed at locations opposite the palmar sensors 722' of the mobilization glove 720.

FIG. 7B is a perspective view of the hardware of a dorsal aspect of a mobilization glove, according to an embodiment of the present disclosure. The dorsal sensors 722" may include inertial units 732 comprising an accelerometer and/or gyroscope. Inertial units 732 indicate angle, velocity, acceleration, and time associated with a given task. In an embodiment, the inertial unit 732 is a MEMS three-axis gyroscope with sensitivity up to ±2000/second and a three-axis accelerometer with a range up to ±16 g. According to an embodiment, an additional sensor 730 is disposed in the web space of the mobilization glove 720. The sensor 730 may comprise a force sensor, an inertial unit, or a combination thereof.

According to an embodiment, the position/motion sensor is at least one of or a combination of a geomagnetic sensor and an acceleration sensor. For example, a three-axis geomagnetic sensor ascertains the direction of geomagnetism, or in other words a geomagnetic vector Vt, given the current orientation of the palmar sensors 722' of the mobilization glove 720 housing the three-axis geomagnetic sensor. A three-axis acceleration sensor ascertains the direction of gravity, or in other words a gravity vector G, given the current orientation of the palmar sensors 722' of the mobilization glove 720 housing the three-axis acceleration sensor in a still state. The gravity vector G matches the downward vertical direction. The gravity vector G likewise may be decomposed into Xs, Ys, and Zs axis components.

Alternatively, or additionally, a gyroscope may be used which is a sensor that detects angular velocity about the three axes Xs, Zs, and Ys (roll, pitch, and yaw), and is able to detect the rotation of an object. In addition, the geomagnetic sensor is able to ascertain the heading in which the object faces, based on a geomagnetic vector as discussed earlier. In an exemplary embodiment, displacement of the palmar sensors 722' is determined, via the processing circuitry of the mobilization glove 720 or the processing circuitry of the head unit, from the inertial data collected from the accelerometer and gyroscope of the inertial unit 732. Evaluating acceleration with respect to time, $\iint_{t_1}^{t_2} a = \Delta l$, where $t_1$ and $t_2$ are the time at two points and a is the acceleration of the mobilization tool, $\Delta l$ represents the displacement of the probe and, therefore, the displacement of the bone of interest. According to an embodiment, and in a non-limiting manner, displacement of the bone of interest is typically quantified in millimeters.

Data from the force sensor 723 and the inertial unit 732 are wirelessly transmitted to the head unit via the wireless communication unit 735. In an embodiment, the wireless communication unit is an IEEE 802.11 b/g compliant WiFi module with an embedded IPv4 TCP/IP stack with an SPI host interface at 16 MHz.

According to an embodiment, the inertial unit 732 of the mobilization glove 720 is calibrated such that a primary axis is aligned with a primary axis of the force sensors 723 of the palmar aspect 721 of the mobilization glove 720.

According to an embodiment, the processing circuitry 736 of the mobilization glove 720 and/or the processing circuitry of the head unit are configured to determine when off-axis force application occurs. In an embodiment, the processing circuitry 736 is further configured to generate an alert in this case. For example, the inertial unit 732 of the mobilization glove 720 records accelerations in three-axes and, therefore, can provide data to the processing circuitry 736 related to accelerations that may exists outside the established axis of the piezo-resistive sensor 723 (i.e., in line with ideal force application). In an embodiment, in order to minimize extraneous pain to the patient and protect the piezo-resistive elements of the mobilization glove 720, the mobilization glove 720 may be further outfitted with a haptic motor 738 in order to alert the user of off-axis load application by providing a small vibratory stimulus to the user. Moreover, a display 733 and a speaker 734 may be controlled to deliver visual and/or audio alerts to the user of off target applications.

To this end, the dorsal aspect 731 of the mobilization glove 720 may comprise a plurality of alert components including but not limited to the display 733, the speaker 734, and the haptic motor 738. The display 733 is one of a variety of flexible displays including but not limited to active-matrix organic light-emitting diode (AMOLED) flexible displays, thereby allowing the display 733 to adapt to the shape of the dorsal aspect 731 of the mobilization glove 720. The speaker 734 is one of a variety of miniature speakers including but not limited to a neodymium magnet design with a Mylar cone. The haptic motor 738 is one of a variety of tactile sensors including but not limited to an Eccentric Rotating mass vibration motor.

The processing circuitry 736 located on a proximal portion of the dorsal aspect 731 of the mobilization glove 720 is configured to receive, process, and transmit data and signals to and from hardware components of the mobilization glove 720 and the head unit.

According to an embodiment, the battery of the mobilization glove 720 is a rechargeable battery 737. The rechargeable battery 737 is a thin film, flexible lithium-polymer rechargeable battery that may be energized by a variety of techniques including but not limited to conduction and induction.

In an exemplary embodiment, following receipt of a prescribed therapy Grade from the head unit, the mobilization glove 720 is placed on the hand of the user. To avoid unintended data recording, a sustained and constant force application at the force sensors 723 of the palmar aspect 721 of the mobilization glove 720 is required in order to begin data recording and transmission. In another embodiment, following location of a bony structure on a bone of the joint of interest, the user may depress the tare toggle 739 to initiate data recording and transmission. As the glove is moved into position on the patient and data recording and transmission begins, force data from the force sensors 723 and inertial data from the inertial units 732 is received, processed and stored by the processing circuitry 736 of the mobilization glove 720 and/or is transmitted via the wireless communication unit 735 to the head unit for processing and storage for longitudinal reference. During operation of the mobilization glove 720, the processing circuitry 736 of the mobilization glove 720 and/or the processing circuitry of the head unit are configured to generate guidance and alerts to the user regarding user performance. For example, as the user displaces a joint in order to achieve a Grade II movement, a visual display on the display 733 may indicate that the current movement is within or without the target Grade. Moreover, the processing circuity may be configured to generate, via the display 733, a visual aid incorporating current force data from the force sensors 723 of the palmar aspect 721 of the mobilization glove 720. If it is determined, via the processing circuitry and according to data from the force sensors 723 and inertial units 732, that the current movement Grade is beyond the prescribed movement Grade, an alert may be generated, via the processing circuitry, to notify the user of the error in mobilization. This alert may be delivered to the user via the speaker 734, disposed on the display 733, or the haptic motor 738 disposed at the base of the thumb in line with the basal carpometacarpal joint.

According to an embodiment, the user may select, via the user interface of the head unit, palmar and dorsal sensors of interest from which to measure and record data. Selected palmar and dorsal sensors may be activated. Concurrently, unselected palmar and dorsal sensors may be deactivated in order to conserve processing power and improve data acquisition.

According to an embodiment, one or more mobilization gloves may be used simultaneously. The sensors of each of the one or more mobilization gloves may be activated or deactivated in part or in whole. In an example, a therapist, using two mobilization gloves, deactivates all sensors on the mobilization glove on their left hand and activates only the sensor of the index finger on the mobilization glove on their right hand.

In another embodiment, each sensor of the mobilization glove may be reviewed after a therapy session and a specific sensor of interest may be isolated according to relative, anticipated, and resultant force levels.

In another embodiment, the head unit may instruct the user of an appropriate sensor to be used for a specific mobilization technique.

Figure 8:
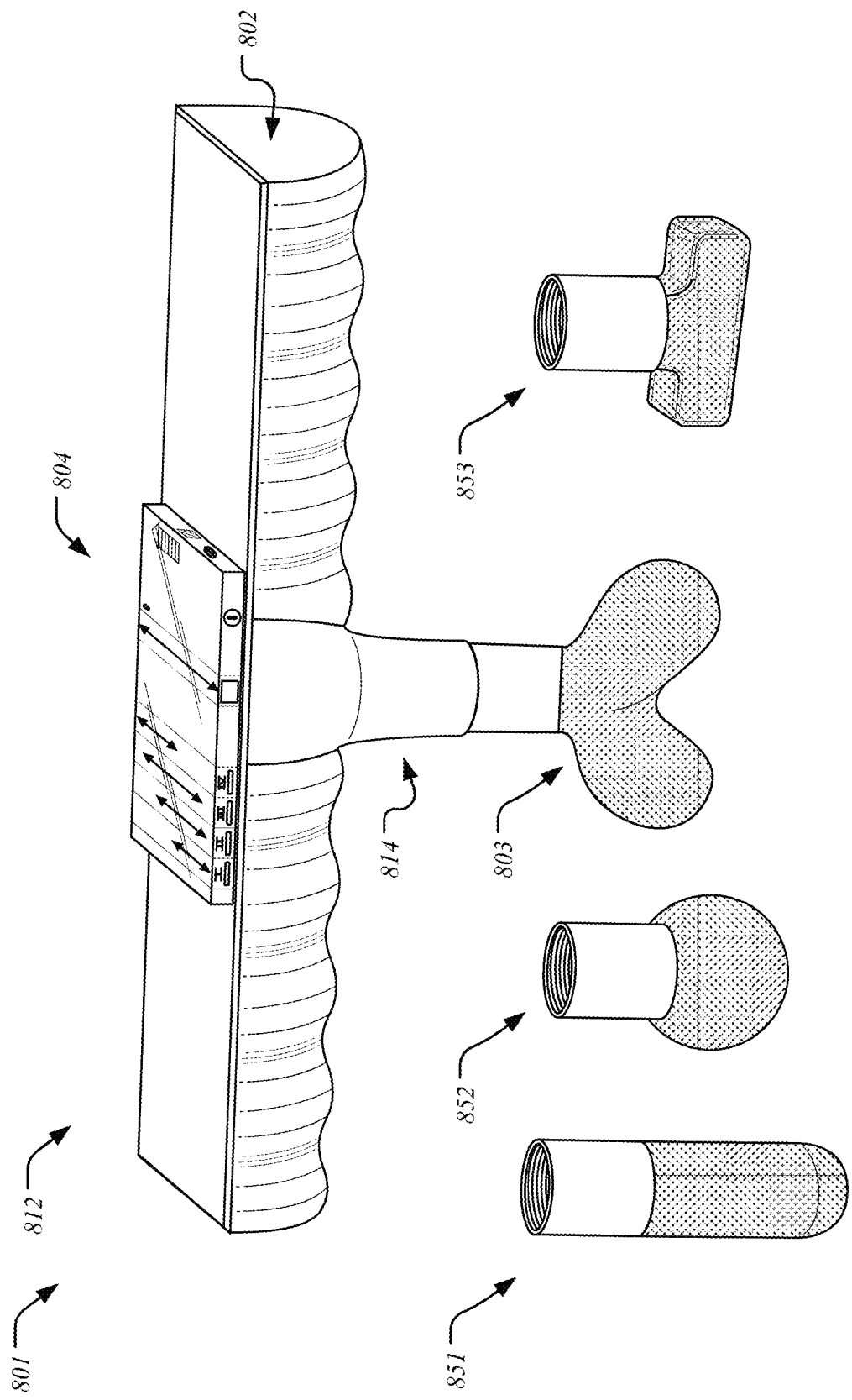
FIG. 8 is a perspective view of a spinal mobilization tool, according to an embodiment of the present disclosure.

FIG. 8 is a perspective view of a spinal mobilization tool, according to an embodiment of the present disclosure. The spinal mobilization tool 812 is an embodiment of the mobilization tool 801. Similarly, the spinal mobilization tool 812 comprises a data unit 804 disposed on a grip 802. The grip 802 is connected to a tool adapter 814, therein further connected to a probe 803. The spinal mobilization tool 812 is designed specifically for mobilization of vertebra in patients suffering from conditions including but not limited to pain and stiffness. In an embodiment, the probe 803 is designed for use in mobilizing the spinous process of the vertebra. In another embodiment, a T probe 853 is designed for mobilization of the facet, or transverse process. In certain embodiments, it is appropriate to modify the contact area between the tool and the patient so that contact forces are reduced at a point. To this end, a hemispherical, cylindrical probe 851 and a spherical probe 852 are designed to distribute load and reduce pain experienced by the patient at the point of contact. These embodiments of the probe 803 are nonlimiting and merely representative of a variety of joint-specific designs.

Figure 9:
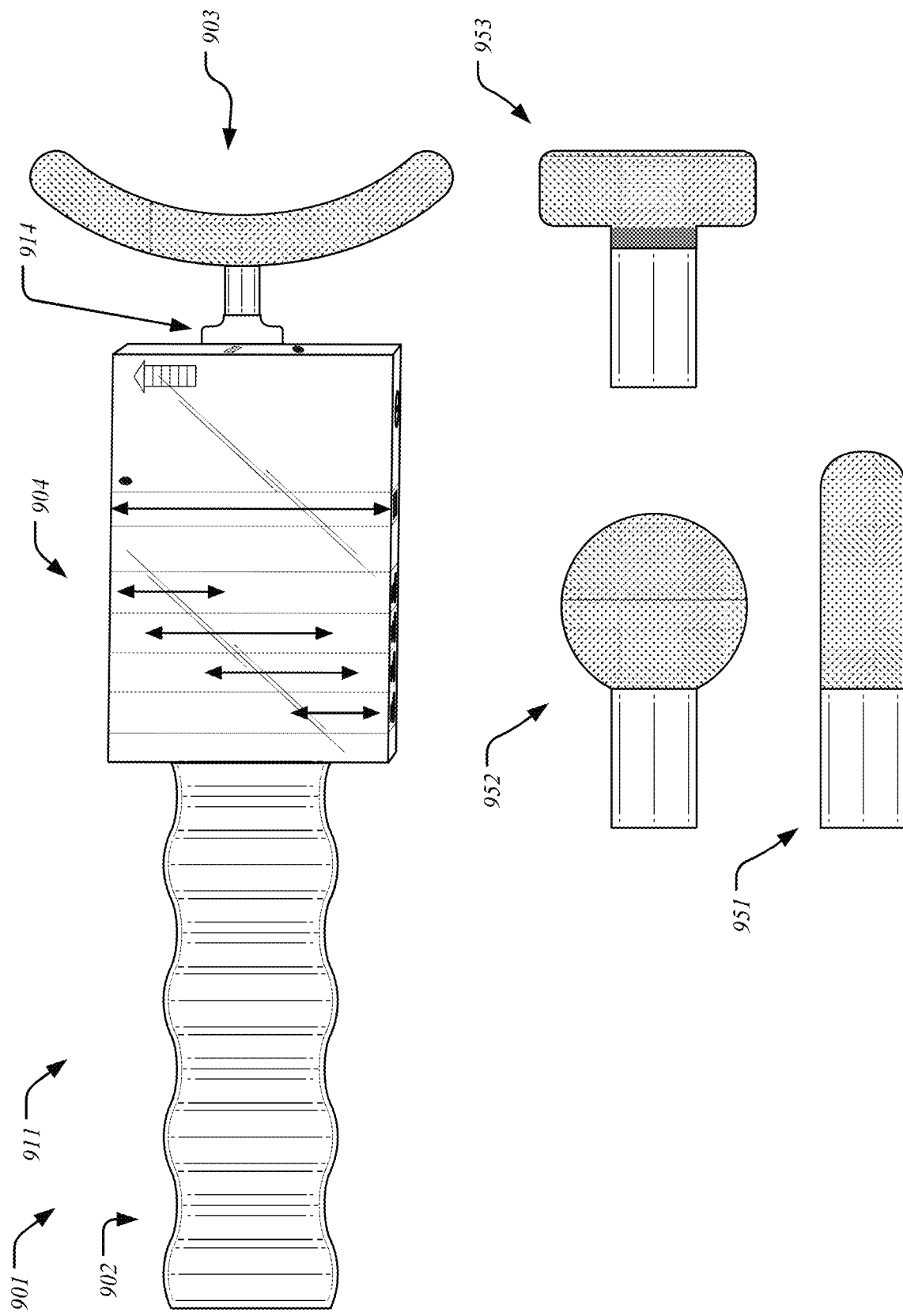
FIG. 9 is a perspective view of an extremity mobilization tool, according to an embodiment of the present disclosure.

FIG. 9 is a perspective view of an extremity mobilization tool, according to an embodiment of the present disclosure. The extremity mobilization tool 911 is an embodiment of the mobilization tool 901. Similarly, the extremity mobilization tool 911 comprises a data unit 904 disposed on a grip 902. In an embodiment, the grip 902 is coincident with the axis of applied force. The grip 902 is connected to a tool adapter 914, therein further connected to a probe 903. The extremity mobilization tool 911 is designed specifically for mobilization of small and large joints of the extremities in patients suffering from conditions including but not limited to pain and stiffness. In an embodiment, the probe 903 is designed for use in mobilizing large joints including but not limited to the knee. In another embodiment, a T probe 953 is designed for mobilization of small joints including but not limited to the elbow. In certain embodiments, it is appropriate to modify the contact area between the tool and the patient so that contact forces are reduced at a point. To this end, a hemispherical, cylindrical probe 951 and a spherical probe 952 are designed to distribute load and reduce pain experienced by the patient at the point of contact. These embodiments of the probe 903 are nonlimiting and merely representative of a variety of joint-specific designs.

Figure 10:
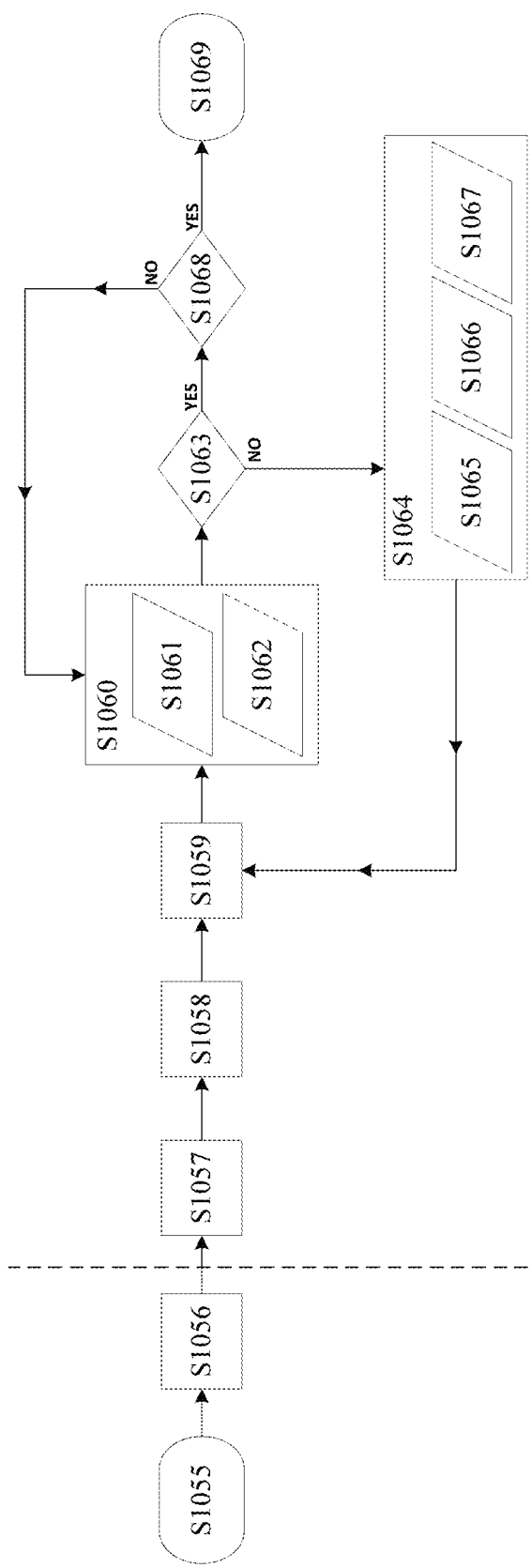
FIG. 10 is a low-level flowchart of an implementation of the mobilization tool and mobilization glove, according to an embodiment of the present disclosure.

FIG. 10 is a low-level flowchart of an implementation of a mobilization tool and mobilization glove. According to an embodiment of the present disclosure. The mobilization tool and the mobilization glove are components of a system that includes the head unit. As the mobilization tool and mobilization glove comprise similar sensing, processing, and display elements, it should be appreciated that, in another embodiment, the mobilization tool may be used independent of the mobilization glove to perform the diagnostic and/or therapeutic functions described below. Further, it should be appreciated that, in another embodiment, the mobilization glove may be used independent of the mobilization tool to perform the diagnostic and/or therapeutic functions described below. In each embodiment, the mobilization tool or the mobilization glove may be in communication with the head unit.

First, the mobilization tool is employed by a prescribing therapist in order to determine the ROM of the patient. To do so, after zeroing the mobilization tool via the tare toggle, a force is applied to a bony structure of a component of the joint to fully displace the joint. At this point, full displacement is set. Following determination of ROM, the processing circuitry of the data unit of the mobilization tool or the processing circuitry of the head unit evaluate the displacement profile of the ROM and assign Grades across the range S1055. Based on performance of the user (e.g., pain, stiffness), the prescribing therapist will recommended a therapy regime beginning with mobilization within one of the assigned Grades S1056. In an embodiment, the prescribing therapist interacts with a user interface of the head unit to record the prescribed Grade of mobilization, wherein the head unit is a personal computer or a smartphone and the processing circuitry of the head unit is configured to implement a software application. For example, for a patient with mild lower back pain, a Grade III mobilization may be prescribed by the prescribing therapist and stored within the memory of the head unit such that it is accessible by the mobilizing therapist. Following subsequent therapy sessions, and according to user performance and progress, the mobilizing therapist may modify the prescribed Grade within the head unit.

According to an embodiment, establishment of the mobilization gradations and initial prescription mobilization is a one-time event. This 'initialization' information is stored to the memory of the head unit to be accessed during therapy sessions S1057. The 'initialization' information includes but is not limited to force data and inertial data (i.e., displacement data). Moreover, 'initialization' data forms a baseline from which subsequent therapy sessions and patient performance will be evaluated.

Next, the mobilizing therapist initiates a therapy session. First, the prescribed Grade is wirelessly communicated to the mobilization glove via the wireless communication unit of the head unit and the mobilization glove S1058. As the patient moves into position and the mobilizing therapist fits the mobilization glove to their hand, data from the force sensors and inertial units is transmitted to and from the processing circuitry of the mobilization glove and/or the processing circuitry of the head unit via the wireless communication unit. The mobilizing therapist positions the glove above the joint and resets data acquisition by one of a variety of methods including but not limited to applying a constant, small pressure to the joint or depressing the tare toggle. In S1059, the mobilizing therapist begins joint mobilization. During mobilization of the joint, sensors are evaluated in context of the target mobilization Grade S1060. Force sensors of the palmar aspect of the mobilization glove generate data related to the resistivity of the sensor in reaction to applied forces S1061. Data from the accelerometers and gyroscopes of the inertial units of the dorsal aspect of the mobilization glove provide displacement information in the context of the applied forces S1062. The processing circuitry of the mobilization glove and/or the processing circuitry of the head unit are configured to receive, process, and transmit the sensed data. Moreover, in the context of the prescribed mobilization Grade, the processing circuitry is configured to evaluate the current mobilization and determine if the mobilization is as prescribed or, if, alternatively, an alert or guidance is required S1063. For example, if a displacement is being applied within a Grade II mobilization although the prescribed mobilization Grade is Grade I, the processing circuitry will determine that an alert is required. If an alert is required, an alert is generated S1064 via the mobilization glove-based output hardware. The mobilization glove-based output hardware includes a speaker to generate an audible tone or phrase to guide the user S1065, a haptic motor at the basal carpometacarpal joint of the thumb to generate vibratory feedback S1066, and a display for conveying simple or complex information to the user S1067. In the example above, upon determining an alert is required, the display may present a simple green or red screen to indicate accuracy of mobilization. Further, the display may present a detailed listing of the current displacement, current force, and target displacement. Moreover, the display may present a Grading scale indicating the current Grade of mobilization in relation to the target mobilization Grade.

Once the mobilizing therapist has been provided feedback, modifications to joint mobilization may be performed S1059. Again, sensed data S1060 from palmar force sensors S1061 and from dorsal inertial units S1062 are received and evaluated by the processing circuitry of the mobilization glove and/or the processing circuitry of the head unit. In the instance where the mobilizing therapist is appropriately displacing the joint of interest S1063, mobilization continues for the remainder of the session, if appropriate S1068. If the therapy session is not finished, the system continuously monitors sensed data S1060 while confirming the accuracy of the applied mobilization of the joint S1063. When the therapy session is determined to be complete S1068, the mobilization glove is removed from the mobilizing therapist hand and the session is finished S1069.

Following completion of the therapy session, the mobilizing therapist may review patient performance via the user interface of the personal computer or smartphone of the head unit. Across subsequent sessions, the force required to reach an equivalent displacement or Grade may be determined to evaluate improvements in patient function. Moreover, future session Grade prescriptions may be decided and recorded within the head unit. According to an embodiment, the output hardware of the mobilization glove and/or the mobilization tool can be used to alert the user to off-axis force applications. The processing circuitry of the mobilization glove, the processing circuitry of the mobilization tool, and/or the processing circuitry of the head unit are configured to receive data from the inertial units of the mobilization tool and/or mobilization glove and to determine a directional vector associated with the plane of the applied force, informing the user when the applied force is not along the plane of an intended force sensor of the mobilization tool and/or mobilization glove.

According to an embodiment, a user may indicate pain level during joint mobilization. This data can be incorporated into the longitudinal history stored in the memory of the head unit and can be used by a prescribing or mobilizing therapist to inform the determination of future prescribed mobilization Grades.

According to an embodiment, alerts generated in response to adverse mobilization of the joint are force-controlled. Based upon previous instances of joint mobilization, an alert may be generated when the mobilizing therapist applies a force X % less than a previously applied force required to achieve a specified Grade of mobilization.

According to an embodiment, longitudinal data recorded during a therapy session, including prescribed mobilization Grades, may be incorporated into home-based robotic therapy devices. In an embodiment, a remote massage apparatus is in wireless communication with a head unit providing instructions regarding the movement of rollers resident in the chair along the spine and the mobilization Grade prescribed to the patient. Further, the patient can record pain during mobilization so that a therapist, local or remote, can modify the prescribe mobilization Grade for future sessions.

Figure 11:
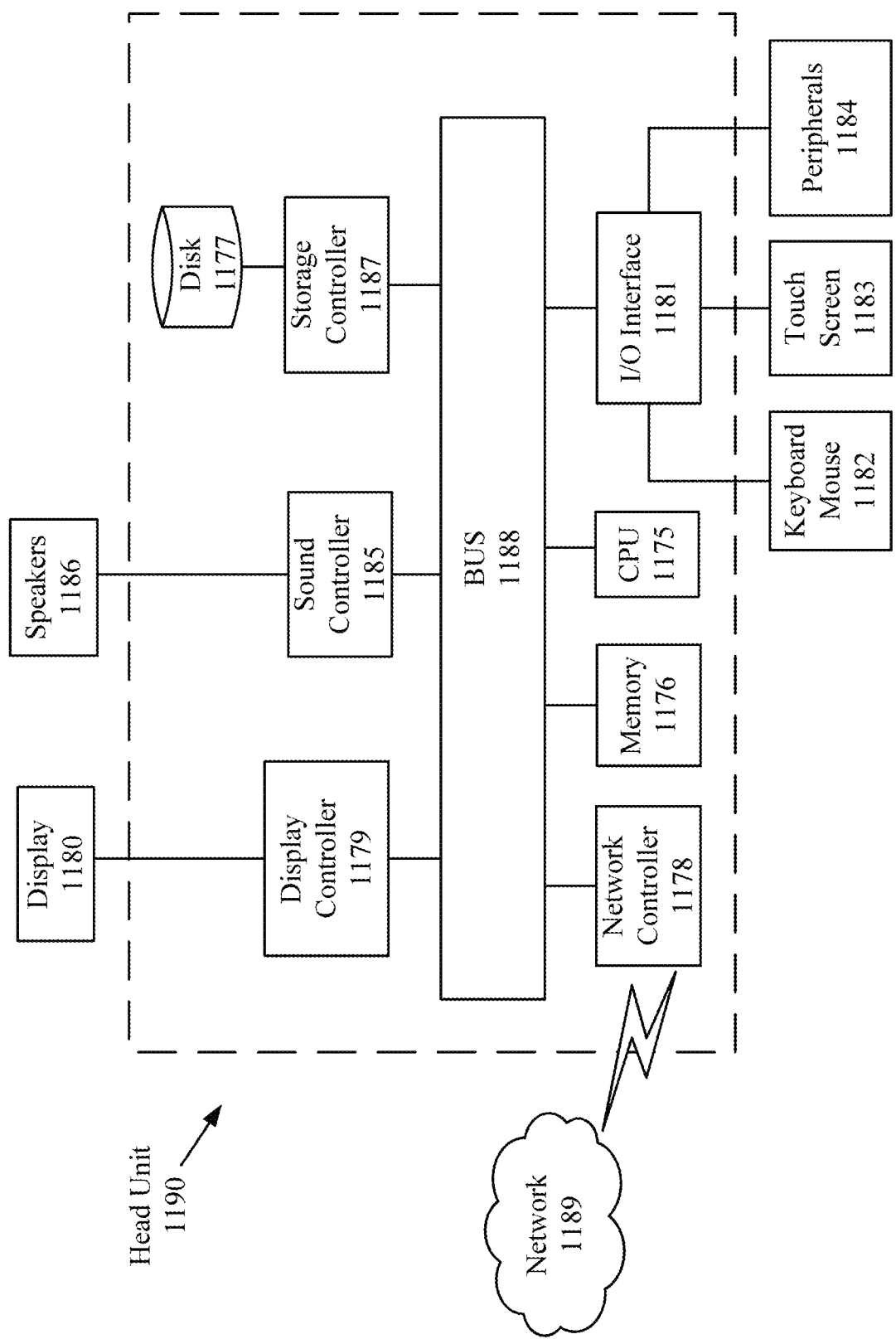
FIG. 11 is a diagram of the hardware of the head unit, according to an embodiment of the present disclosure.

Next, a hardware description of the head unit according to exemplary embodiments is described with reference to FIG. 11. In FIG. 11, the head unit includes a CPU 1175 which performs the processes described above. The process data and instructions may be stored in memory 1176. These processes and instructions may also be stored on a storage medium disk 1177 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the head unit communicates, such as a server or computer. Further, the claimed advancements may be provided as a utility application, background daemon, or component of an operating system, or combination thereof, executing in conjunction with CPU 1175 and an operating system such as Microsoft Windows 7, UNIX, Solaris, LINUX, Apple MAC-OS and other systems known to those skilled in the art.

The hardware elements in order to achieve the head unit may be realized by various circuitry elements, known to those skilled in the art. For example, CPU 1175 may be a Xenon or Core processor from Intel of America or an Opteron processor from AMD of America, or may be other processor types that would be recognized by one of ordinary skill in the art. Alternatively, the CPU 1175 may be implemented on an FPGA, ASIC, PLD or using discrete logic circuits, as one of ordinary skill in the art would recognize. Further, CPU 1175 may be implemented as multiple processors cooperatively working in parallel to perform the instructions of the inventive processes described above.

The head unit in FIG. 11 also includes a network controller 1178, such as an Intel Ethernet PRO network interface card from Intel Corporation of America, for interfacing with network 1189. As can be appreciated, the network 1189 can be a public network, such as the Internet, or a private network such as an LAN or WAN network, or any combination thereof and can also include PSTN or ISDN subnetworks. The network 1189 can also be wired, such as an Ethernet network, or can be wireless such as a cellular network including EDGE, 3G and 4G wireless cellular systems. The wireless network can also be WiFi, Bluetooth, or any other wireless form of communication that is known.

The head unit further includes a display controller 1179, such as a NVIDIA GeForce GTX or Quadro graphics adaptor from NVIDIA Corporation of America for interfacing with display 1180, such as a Hewlett Packard HPL2445w LCD monitor. A general purpose I/O interface 1181 interfaces with a keyboard and/or mouse 1182 as well as a touch screen panel 1183 on or separate from display 1180. General purpose I/O interface also connects to a variety of peripherals 1184 including printers and scanners, such as an OfficeJet or DeskJet from Hewlett Packard.

A sound controller 1185 is also provided in the head unit, such as Sound Blaster X-Fi Titanium from Creative, to interface with speakers/microphone 1186 thereby providing sounds and/or music.

The general purpose storage controller 1187 connects the storage medium disk 1177 with communication bus 1188, which may be an ISA, EISA, VESA, PCI, or similar, for interconnecting all of the components of the head unit. A description of the general features and functionality of the display 1180, keyboard and/or mouse 1182, as well as the display controller 1179, storage controller 1187, network controller 1178, sound controller 1185, and general purpose I/O interface 1181 is omitted herein for brevity as these features are known.

Figure 12:
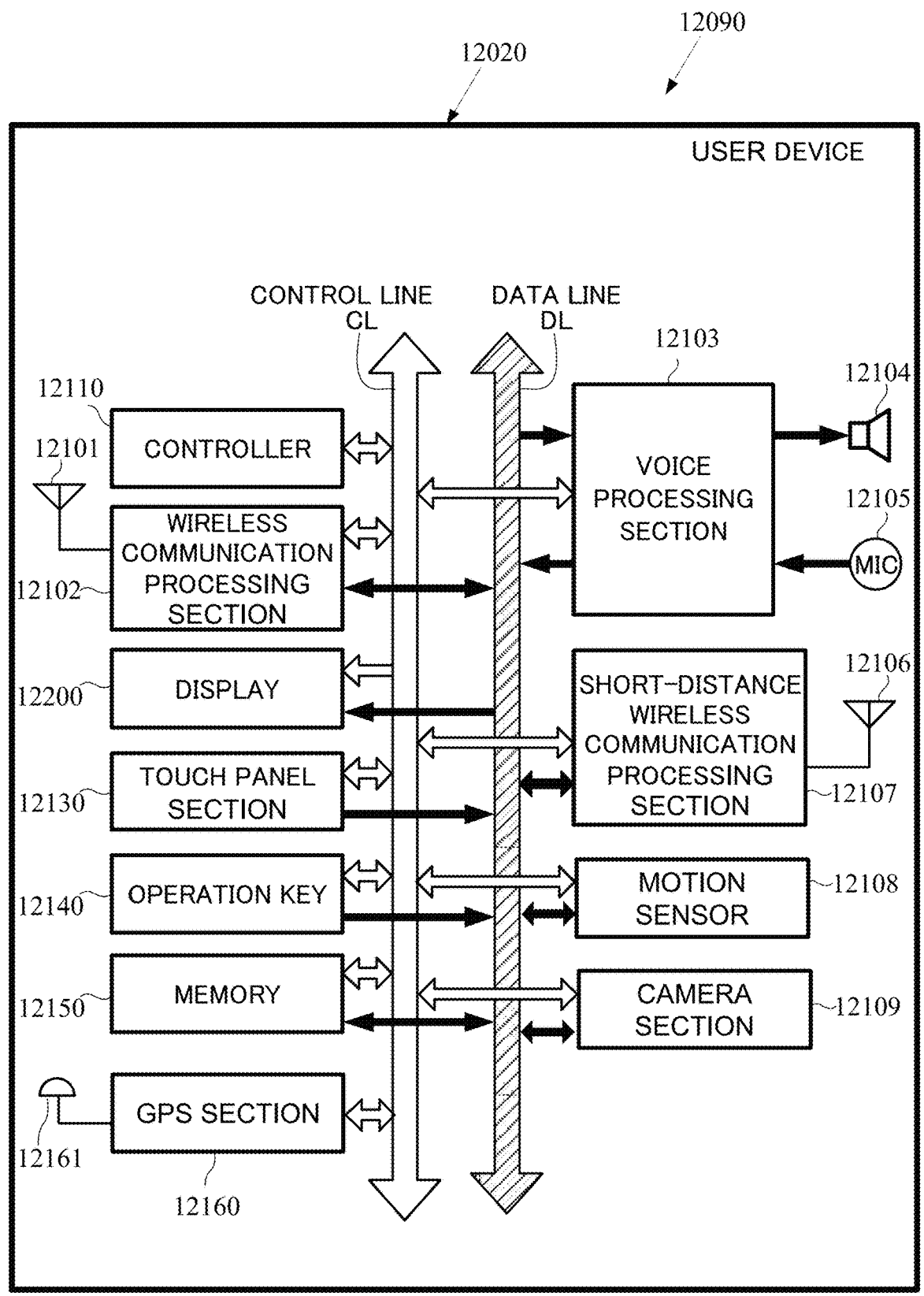
FIG. 12 is a diagram illustrating an exemplary head unit, according to an embodiment of the present disclosure.

FIG. 12 is a detailed block diagram illustrating an exemplary head unit, according to an embodiment of the present disclosure. In an embodiment, the head unit 12090 is a user device 12020. In certain embodiments, user device 12020 may be a smartphone. However, the skilled artisan will appreciate that the features described herein may be adapted to be implemented on other devices (e.g., a laptop, a tablet, a server, an e-reader, a camera, a navigation device, etc.). The exemplary user device 12020 includes a controller 12110 and a wireless communication processor 12102 connected to an antenna 12101. A speaker 12104 and a microphone 12105 are connected to a voice processor 12103.

The controller 12110 may include one or more Central Processing Units (CPUs), and may control each element in the user device 12020 to perform functions related to communication control, audio signal processing, control for the audio signal processing, still and moving image processing and control, and other kinds of signal processing. The controller 12110 may perform these functions by executing instructions stored in a memory 12150. Alternatively or in addition to the local storage of the memory 12150, the functions may be executed using instructions stored on an external device accessed on a network or on a non-transitory computer readable medium.

The memory 12150 includes but is not limited to Read Only Memory (ROM), Random Access Memory (RAM), or a memory array including a combination of volatile and non-volatile memory units. The memory 12150 may be utilized as working memory by the controller 12110 while executing the processes and algorithms of the present disclosure. Additionally, the memory 12150 may be used for long-term storage, e.g., of image data and information related thereto. The memory 12150 may be configured to store the battle view information, operation view information and list of commands.

The user device 12020 includes a control line CL and data line DL as internal communication bus lines. Control data to/from the controller 12110 may be transmitted through the control line CL. The data line DL may be used for transmission of voice data, display data, etc.

The antenna 12101 transmits/receives electromagnetic wave signals between base stations for performing radio-based communication, such as the various forms of cellular telephone communication. The wireless communication processor 12102 controls the communication performed between the user device 12020 and other external devices via the antenna 12101. For example, the wireless communication processor 12102 may control communication between base stations for cellular phone communication. The speaker 12104 emits an audio signal corresponding to audio data supplied from the voice processor 12103. The microphone 12105 detects surrounding audio and converts the detected audio into an audio signal. The audio signal may then be output to the voice processor 12103 for further processing. The voice processor 12103 demodulates and/or decodes the audio data read from the memory 12150 or audio data received by the wireless communication processor 12102 and/or a short-distance wireless communication processor 12107. Additionally, the voice processor 12103 may decode audio signals obtained by the microphone 12105. The exemplary user device 12020 may also include a display 12120, a touch panel 12130, an operation key 12140, and a short-distance communication processor 12107 connected to an antenna 12106. The display 12120 may be a Liquid Crystal Display (LCD), an organic electroluminescence display panel, or another display screen technology. In addition to displaying still and moving image data, the display 12120 may display operational inputs, such as numbers or icons which may be used for control of the user device 12020. The display 12120 may additionally display a GUI for a user to control aspects of the user device 12020 and/or other devices. Further, the display 12120 may display characters and images received by the user device 12020 and/or stored in the memory 12150 or accessed from an external device on a network. For example, the user device 12020 may access a network such as the Internet and display text and/or images transmitted from a Web server.

The touch panel 12130 may include a physical touch panel display screen and a touch panel driver. The touch panel 12130 may include one or more touch sensors for detecting an input operation on an operation surface of the touch panel display screen. The touch panel 12130 also detects a touch shape and a touch area. Used herein, the phrase "touch operation" refers to an input operation performed by touching an operation surface of the touch panel display with an instruction object, such as a finger, thumb, or stylus-type instrument. In the case where a stylus or the like is used in a touch operation, the stylus may include a conductive material at least at the tip of the stylus such that the sensors included in the touch panel 12130 may detect when the stylus approaches/contacts the operation surface of the touch panel display (similar to the case in which a finger is used for the touch operation). One or more of the display 12120 and the touch panel 12130 are examples of a touch panel display.

In certain aspects of the present disclosure, the touch panel 12130 may be disposed adjacent to the display 12120 (e.g., laminated) or may be formed integrally with the display 12120. For simplicity, the present disclosure assumes the touch panel 12130 is formed integrally with the display 12120 and therefore, examples discussed herein may describe touch operations being performed on the surface of the display 12120 rather than the touch panel 12130. However, the skilled artisan will appreciate that this is not limiting.

For simplicity, the present disclosure assumes the touch panel 12130 is a capacitance-type touch panel technology. However, it should be appreciated that aspects of the present disclosure may easily be applied to other touch panel types (e.g., resistance-type touch panels) with alternate structures. In certain aspects of the present disclosure, the touch panel 12130 may include transparent electrode touch sensors arranged in the X-Y direction on the surface of transparent sensor glass.

The touch panel driver may be included in the touch panel 12130 for control processing related to the touch panel 12130, such as scanning control. For example, the touch panel driver may scan each sensor in an electrostatic capacitance transparent electrode pattern in the X-direction and Y-direction and detect the electrostatic capacitance value of each sensor to determine when a touch operation is performed. The touch panel driver may output a coordinate and corresponding electrostatic capacitance value for each sensor. The touch panel driver may also output a sensor identifier that may be mapped to a coordinate on the touch panel display screen. Additionally, the touch panel driver and touch panel sensors may detect when an instruction object, such as a finger is within a predetermined distance from an operation surface of the touch panel display screen. That is, the instruction object does not necessarily need to directly contact the operation surface of the touch panel display screen for touch sensors to detect the instruction object and perform processing described herein. For example, in certain embodiments, the touch panel 12130 may detect a position of a user's finger around an edge of the display panel 12120 (e.g., gripping a protective case that surrounds the display/touch panel). Signals may be transmitted by the touch panel driver, e.g. in response to a detection of a touch operation, in response to a query from another element based on timed data exchange, etc.

The touch panel 12130 and the display 12120 may be surrounded by a protective casing, which may also enclose the other elements included in the user device 12020. In certain embodiments, a position of the user's fingers on the protective casing (but not directly on the surface of the display 12120) may be detected by the touch panel 12130 sensors. Accordingly, the controller 12110 may perform display control processing described herein based on the detected position of the user's fingers gripping the casing. For example, an element in an interface may be moved to a new location within the interface (e.g., closer to one or more of the fingers) based on the detected finger position.

Further, in certain embodiments, the controller 12110 may be configured to detect which hand is holding the user device 12020, based on the detected finger position. For example, the touch panel 12130 sensors may detect a plurality of fingers on the left side of the user device 12020 (e.g., on an edge of the display 12120 or on the protective casing), and detect a single finger on the right side of the user device 12020. In this exemplary scenario, the controller 12110 may determine that the user is holding the user device 12020 with his/her right hand because the detected grip pattern corresponds to an expected pattern when the user device 12020 is held only with the right hand.

The operation key 12140 may include one or more buttons or similar external control elements, which may generate an operation signal based on a detected input by the user. In addition to outputs from the touch panel 12130, these operation signals may be supplied to the controller 12110 for performing related processing and control. In certain aspects of the present disclosure, the processing and/or functions associated with external buttons and the like may be performed by the controller 12110 in response to an input operation on the touch panel 12130 display screen rather than the external button, key, etc. In this way, external buttons on the user device 12020 may be eliminated in lieu of performing inputs via touch operations, thereby improving water-tightness.

The antenna 12106 may transmit/receive electromagnetic wave signals to/from other external apparatuses, and the short-distance wireless communication processor 12107 may control the wireless communication performed between the other external apparatuses. Bluetooth, IEEE 802.11, and near-field communication (NFC) are non-limiting examples of wireless communication protocols that may be used for inter-device communication via the short-distance wireless communication processor 12107.

The user device 12020 may include a motion sensor 12108. The motion sensor 12108 may detect features of motion (i.e., one or more movements) of the user device 12020. For example, the motion sensor 12108 may include an accelerometer to detect acceleration, a gyroscope to detect angular velocity, a geomagnetic sensor to detect direction, a geo-location sensor to detect location, etc., or a combination thereof to detect motion of the user device 12020. In certain embodiments, the motion sensor 12108 may generate a detection signal that includes data representing the detected motion. For example, the motion sensor 12108 may determine a number of distinct movements in a motion (e.g., from start of the series of movements to the stop, within a predetermined time interval, etc.), a number of physical shocks on the user device 12020 (e.g., a jarring, hitting, etc., of the electronic device), a speed and/or acceleration of the motion (instantaneous and/or temporal), or other motion features. The detected motion features may be included in the generated detection signal. The detection signal may be transmitted, e.g., to the controller 12110, whereby further processing may be performed based on data included in the detection signal. The motion sensor 12108 can work in conjunction with a Global Positioning System (GPS) section 12160. The information of the present position detected by the GPS section 12160 is transmitted to the controller 12110. An antenna 12161 is connected to the GPS section 12160 for receiving and transmitting signals to and from a GPS satellite.

The user device 12020 may include a camera section 12109, which includes a lens and shutter for capturing photographs of the surroundings around the user device 12020. In an embodiment, the camera section 12109 captures surroundings of an opposite side of the user device 12020 from the user. The images of the captured photographs can be displayed on the display panel 12120. A memory section saves the captured photographs. The memory section may reside within the camera section 12109 or it may be part of the memory 12150. The camera section 12109 can be a separate feature attached to the user device 12020 or it can be a built-in camera feature.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An apparatus for joint mobilization, comprising:
   one or more sensors;
   one or more alert components; and
   processing circuitry configured to:
   receive, from the one or more sensors, a first sensed data in response to a first applied motion to a joint of a patient, the first applied motion being applied by an applicator of the apparatus,
   determine, based upon the first sensed data, a range of motion of the joint of the patient,
   assign, based upon the determined range of motion of the joint of the patient, mobilization gradations corresponding to relative magnitudes of motion,
   receive, from the one or more sensors, a second sensed data in response to a second applied motion to the joint of the patient, the second applied motion being applied by the applicator of the apparatus,
   determine, based upon the second sensed data and the determined range of motion of the joint of the patient, a relative magnitude of the second sensed data of the second applied motion to the joint of the patient, and
   generate, based upon a comparison of the relative magnitude of the second sensed data of the second applied motion to the joint of the patient and the assigned mobilization gradations, a signal to one or more alert components indicating with which mobilization gradation the second applied motion should be associated.

2. The apparatus according to claim 1, wherein the one or more sensors include force sensors, accelerometers, gyroscopes, or a combination thereof.

3. The apparatus according to claim 2, wherein the force sensors include strain gauges, piezo-resistive elements, or a combination thereof.

4. The apparatus according to claim 1, wherein the first sensed data and the second sensed data are displacement data.

5. The apparatus according to claim 1, wherein the one or more alert components includes a light-emitting diode, a haptic motor, or a combination thereof.

6. The apparatus according to claim 1, wherein the processing circuitry is further configured to:
   identify, based upon the first sensed data, a target motion of the determined range of motion of the joint of the patient, the identified target motion corresponding to a mobilization gradation of the assigned mobilization gradations,
   determine, based upon a comparison of the second sensed data and the identified target motion, an accuracy of the second applied motion to the joint of the patient, and generate, based upon the determined accuracy, a signal to the one or more alert components indicating the accuracy of the second applied motion to the joint of the patient.

7. A method for joint mobilization, comprising:
receiving, by processing circuitry and from one or more sensors, a first sensed data in response to a first applied motion to a joint of a patient, the first applied motion being applied by an applicator;
determining, by the processing circuitry and based upon the first sensed data, a range of motion of the joint of the patient;
assigning, by the processing circuitry and based on the determined range of motion of the joint of the patient, mobilization gradations corresponding to relative magnitudes of motion;
receiving, by the processing circuitry and from the one or more sensors, a second sensed data in response to a second applied motion to the joint of the patient, the second applied motion being applied by the applicator;
determining, by the processing circuitry and based upon the second sensed data and the determined range of motion of the joint of the patient, a relative magnitude of the second sensed data of the second applied motion to the joint of the patient; and
generating, by the processing circuitry and based upon the relative magnitude of the second sensed data of the second applied motion to the joint of the patient and the assigned mobilization gradations, a signal to one or more alert components indicating with which mobilization gradation the second applied motion should be associated.

8. The method according to claim 7, wherein the one or more sensors include force sensors, accelerometers, gyroscopes, or a combination thereof.

9. The method according to claim 8, wherein the force sensors include strain gauges, piezo-resistive elements, or a combination thereof.

10. The method according to claim 7, wherein the first sensed data and the second sensed data are displacement data.

11. The method according to claim 7, wherein the one or more alert components includes a light-emitting diode, a haptic motor, or a combination thereof.

12. The method according to claim 7, further comprising:
identifying, by the processing circuitry and based upon the first sensed data, a target motion of the determined range of motion of the joint of the patient, the identified target motion corresponding to a mobilization gradation of the assigned mobilization gradations;
determining, by the processing circuitry and based upon a comparison of the second sensed data and the identified target motion, an accuracy of the second applied motion to the joint of the patient; and
generating, by the processing circuitry and based upon the determined accuracy, a signal to the one or more alert components indicating the accuracy of the second applied motion to the joint of the patient.

13. The apparatus according to claim 1, further comprising
a grip at a first end of a tool, and
a probe having a bilobar shape and arranged at a second end of the tool, the probe being configured for contact with the joint of the patient during application of the first applied motion and the second applied motion, wherein the one or more sensors are coupled to the probe at the second end of the tool,
the processing circuitry is disposed within a housing coupled to the tool, and
the one or more alert components include an indicator of which mobilization gradation the second applied motion has been associated with.

14. A system for joint mobilization, comprising:
a mobilization tool having a first set of one or more sensors and first processing circuitry configured to transmit sensed data acquired by the first set of one or more sensors; and
a head unit having second processing circuitry configured to:
receive, from the first set of one or more sensors via the first processing circuitry, a first sensed data in response to a first applied motion to a joint of a patient, the first applied motion being applied by the mobilization tool,
determine, based upon the first sensed data, a range of motion of the joint of the patient, and
assign, based upon the determined range of motion of the joint of the patient, mobilization gradations corresponding to relative magnitudes of motion.

15. The system according to claim 14, further comprising:
a mobilization glove having a second set of one or more sensors and third processing circuitry, wherein the second processing circuitry of the head unit is further configured to:
receive, from the second set of one or more sensors via the third processing circuitry, a second sensed data in response to a second applied motion to the joint of the patient, the second applied motion being applied by the mobilization glove,
determine, based upon the second sensed data and the determined range of motion of the joint of the patient, a relative magnitude of the second sensed data of the second applied motion to the joint of the patient, and
generate, based upon a comparison of the relative magnitude of the second sensed data of the second applied motion to the joint of the patient and the assigned mobilization gradations, a signal to one or more alert components indicating with which mobilization grade the second applied motion should be associated.

16. The system according to claim 15, wherein the one or more sensors include force sensors, accelerometers, gyroscopes, or a combination thereof.

17. The system according to claim 16, wherein the force sensors include strain gauges, piezo-resistive elements, or a combination thereof.

18. The system according to claim 15, wherein the first sensed data and the second sensed data are displacement data.

19. The system according to claim 15, wherein the one or more alert components includes a light-emitting diode, a display, a haptic motor, or a combination thereof.

20. The system according to claim 15, wherein the second processing circuitry is further configured to:
identify, based upon the first sensed data, a target motion of the determined range of motion of the joint of the patient, the identified target motion corresponding to a mobilization gradation of the assigned mobilization gradations, determine, based upon a comparison of the second sensed data and the identified target motion, an accuracy of the second applied motion to the joint of the patient, and generate, based upon the determined accuracy, a signal to the one or more alert components indicating the accuracy of the second applied motion to the joint of the patient.

* * * * *